US011307204B2

(12) United States Patent
Ezrin

(10) Patent No.: US 11,307,204 B2
(45) **Date of Patent: *Apr. 19, 2022**

(54) 5-ALA FOR DETECTION OF BRAIN TUMORS

(71) Applicant: PIOMA, INC., Miami, FL (US)

(72) Inventor: Alan M. Ezrin, Miami, FL (US)

(73) Assignee: PIOMA, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/435,186

(22) Filed: Jun. 7, 2019

(65) Prior Publication Data

US 2020/0124607 A1 Apr. 23, 2020

Related U.S. Application Data

(60) Continuation of application No. 15/277,982, filed on Sep. 27, 2016, now abandoned, which is a division of application No. 13/838,895, filed on Mar. 15, 2013, now Pat. No. 9,493,810.

(60) Provisional application No. 61/656,945, filed on Jun. 7, 2012.

(51) Int. Cl.

| | |
|---|---|
| ***G01N 33/574*** | (2006.01) |
| ***C12Q 1/26*** | (2006.01) |
| ***C12Q 1/48*** | (2006.01) |
| ***C12Q 1/527*** | (2006.01) |
| ***G01N 33/94*** | (2006.01) |

(52) U.S. Cl.

CPC ......... *G01N 33/57484* (2013.01); *C12Q 1/26* (2013.01); *C12Q 1/48* (2013.01); *C12Q 1/527* (2013.01); *C12Y 103/03* (2013.01); *G01N 33/94* (2013.01); *G01N 2333/90206* (2013.01)

(58) Field of Classification Search

CPC ............. G01N 33/57484; G01N 33/94; G01N 2333/90206; C12Q 1/26; C12Q 1/48; C12Q 1/527; C12Y 103/03

USPC ........................................................... 435/15

See application file for complete search history.

(56) References Cited

U.S. PATENT DOCUMENTS

| | | | |
|---|---|---|---|
| 5,407,808 | A | 4/1995 | Halling et al. |
| 6,066,628 | A | 5/2000 | Stojiljkovic et al. |
| 7,611,839 | B2 | 11/2009 | Twine et al. |
| 9,493,810 | B2 | 11/2016 | Ezrin |
| 2002/0183386 | A1 | 12/2002 | Gierskcky et al. |
| 2008/0108701 | A1 | 5/2008 | Okura et al. |
| 2008/0260650 | A1 | 10/2008 | Tawakol et al. |
| 2010/0184671 | A1 | 7/2010 | Van Den Oudenrijn et al. |
| 2011/0195491 | A1 | 8/2011 | Selinfreund et al. |
| 2013/0330753 | A1 | 12/2013 | Ezrin |
| 2017/0192005 | A1 | 7/2017 | Ezrin |

FOREIGN PATENT DOCUMENTS

| | | |
|---|---|---|
| EP | 2347703 A1 | 7/2011 |

OTHER PUBLICATIONS

Anand et al., "Low-dose Methotrexate Enhances Aminolevulinate-based Photodynamic Therapy in Skin Carcinoma Cells in-vitro and in-vivo", Clinical Cancer Research, vol. 15, No. 10, May 15, 2009, pp. 3333-3343.

Casas et al., "Topical and Intratumoral Photodynamic Therapy with 5-Aminolevulinic Acid in a Subcutaneous Murine Mammary Adenocarcinoma", Cancer Letters, vol. 141, Jul. 1, 1999, pp. 29-38.

Dragovic et al., "Sizing and Phenotyping of Cellular Vesicles Using Nanoparticle Tracking Analysis", Nanomedicine: Nanotechnology, Biology, and Medicine, vol. 7, 2011, pp. 780-788.

Drugs.com, Medical Term: Microparticle, Accessed online Jan. 7, 2015 at: www.drugs.com/dict/microparticle.html.

Extended European Search Report received for European Patent Application No. 138008529, dated Nov. 16, 2015, 9 pages.

International Search Report and Written Opinion received for PCT Patent Application No. PCT/US2013/044351, dated Oct. 24, 2013, 10 pages.

International Preliminary Report on Patentability received for PCT Patent Application No. PCT/US2013/044351, dated Dec. 18, 2014, 9 pages.

Ishizuka et al., Novel development of 5-aminolevurinic acid (ALA) in cancer diagnoses and therapy, International Immunopharmacology 11 (Mar. 2011) 358-365.

Ishizuka et al., "Porphyrins in Urine After Administration of 5-aminolevulinic Acid as a Potential Tumor Marker" Photodiagnosis and Photodynamic Therapy, vol. 8, Dec. 2011, pp. 328-331.

Lee et al., "Microvesicles as Mediators of Intercellular Communication in Cancer—The Emerging Science of Cellular 'Debris'", Seminars in Immunopathology, vol. 33, Sep. 2011, pp. 455-467.

Medac, Gliolan, Product information Sheet, revised Feb. 2014, accessible online at: www.medacuk.com/assets/files/SPC%20Gliolan%2002-2014.

Muralidharan-Chari et al., Microvesicles: mediators of extracellular communication during cancer progression, Journal of Cell Science, 123 (10), 1603-1611 (2010).

Rak, Janusz, "Microparticles in Cancer", Seminars in Thrombosis and Hemostasis, vol. 36, No. 8, 2010, pp. 888-906.

Roberts et al., "Coregistered Fluorescence-Enhanced Tumor Resection of Malignant Glioma: Relationships between Delta-Aminolevulinic Acid-Induced Protoporphyrin IX Fluorescence, Magnetic Resonance Imaging Enhancement, and Neuropathological Parameters", Journal of Neurosurgery, vol. 114, No. 3, Mar. 2011, pp. 595-603.

Safaei et al., "Abnormal Lysosomal Trafficking and Enhanced Exosomal Export of Cisplatin in Drug-resistant Human Ovarian Carcinoma Cells" Molecular Cancer Therapeutics, vol. 4, No. 10, Oct. 2005, pp. 1595-1604.

(Continued)

*Primary Examiner* — Jennifer M. H. Tichy

(74) *Attorney, Agent, or Firm* — Cooley LLP

(57) ABSTRACT

The present disclosure relates to methods for detecting brain tumors and assessing the recurrence of such tumors by administering a pharmaceutical composition comprising 5-aminolevulinic acid (5-ALA) and detecting the conversion of 5-ALA to protoporphyrin IX (PPIX) associated with brain-derived microparticles.

13 Claims, 16 Drawing Sheets
(16 of 16 Drawing Sheet(s) Filed in Color)

(56) References Cited

OTHER PUBLICATIONS

Shedden et al., "Expulsion of Small Molecules in Vesicles Shed by Cancer Cells: Association with Gene Expression and Chemosensitivity Profiles" Cancer Resarch, vol. 63, Aug. 1, 2003, pp. 4331-4337.
Valdes et al., Combined fluorescence and reflectance spectroscopy for in vivo quantification of cancer biomarkers in low- and high-grade glioma surgery, Journal of Biomedical Optics 16(11), 116007 (Nov. 2011).
Valdes et al., "Gadolinium and 5-Aminolevulinic Acid-Induced Protoporphyrin IX Levels in Human Gliomas: An Ex Vivo Quantitative Study to Correlate Protoporphyrin IX Levels and Blood-Brain Barrier Breakdown", Journal of Neuropathology and Experimental Neurology, vol. 71, No. 9, Sep. 2012, pp. 806-813.

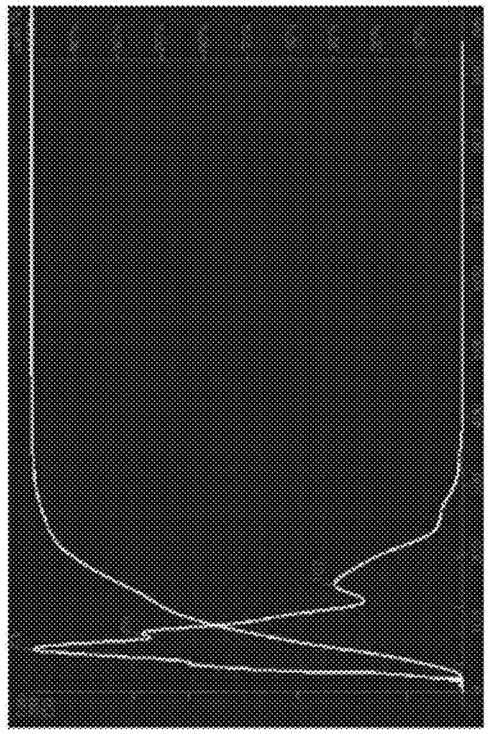
FIG. 3A
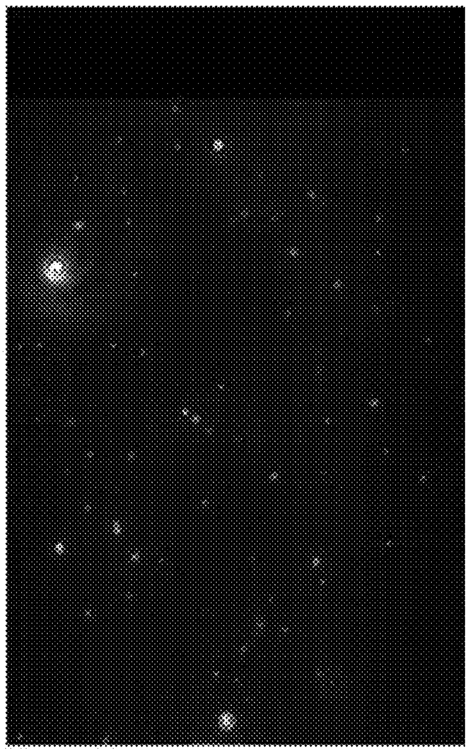
FIG. 3B
FIG. 3C
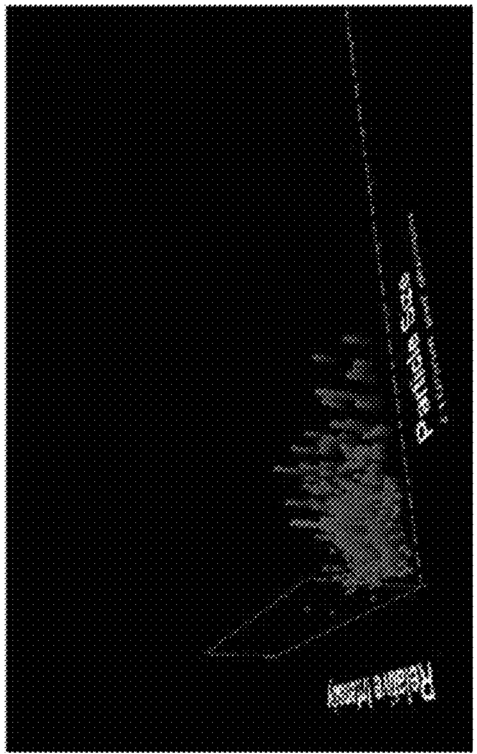
FIG. 3D

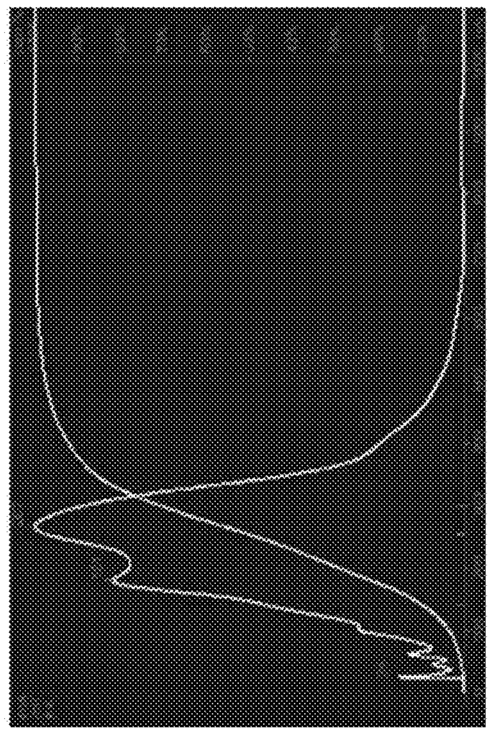
FIG. 5A
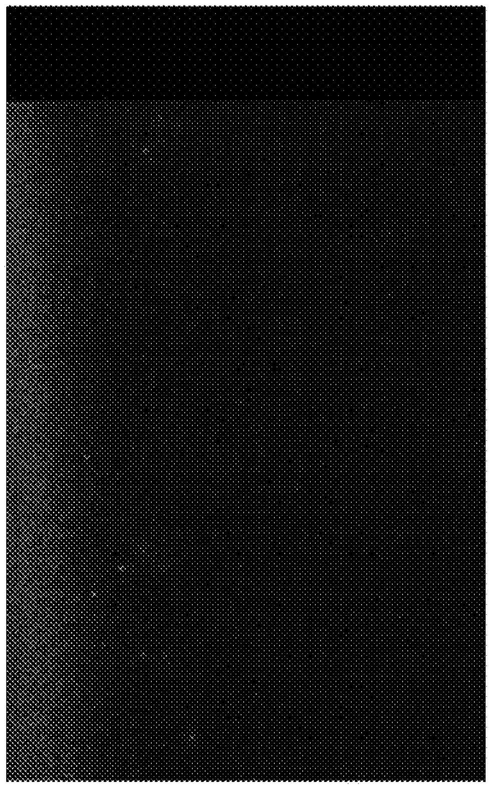
FIG. 5B
FIG. 5C
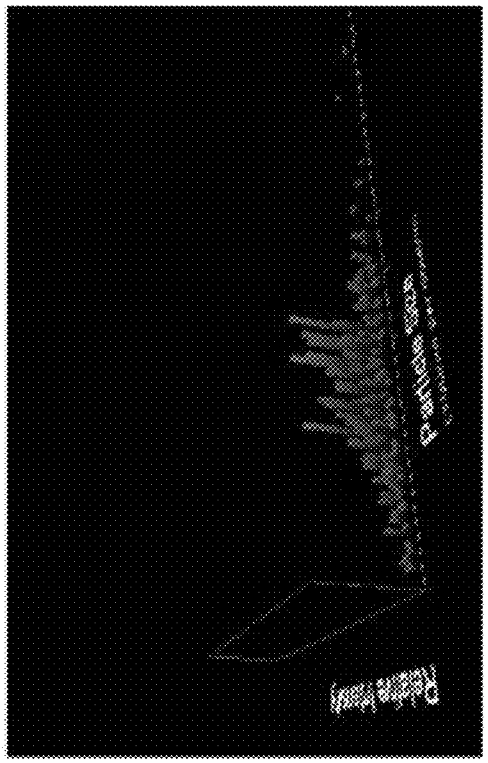
FIG. 5D

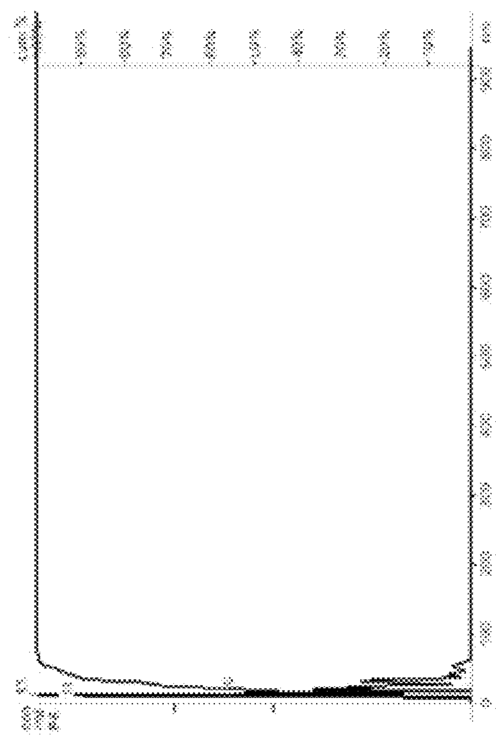
FIG. 10A
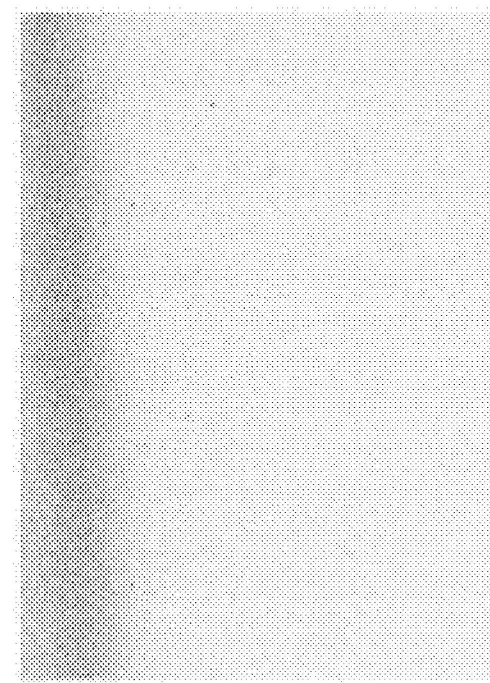
FIG. 10B
FIG. 10C
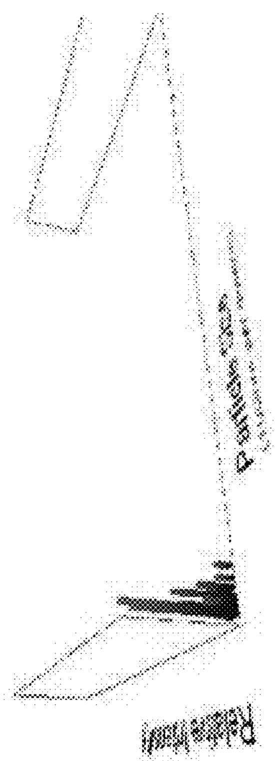
FIG. 10D

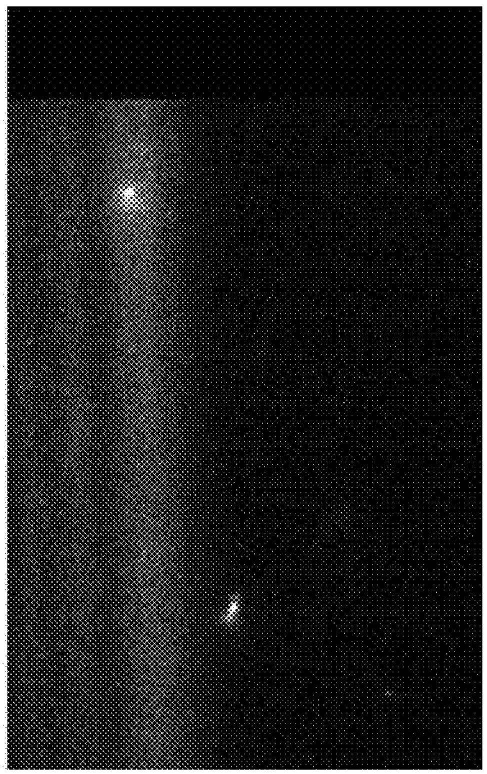
FIG. 11B
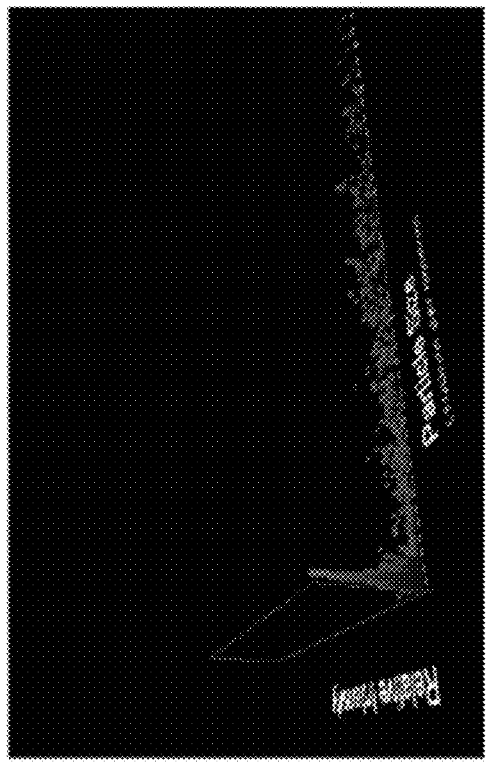
FIG. 11D
FIG. 11A
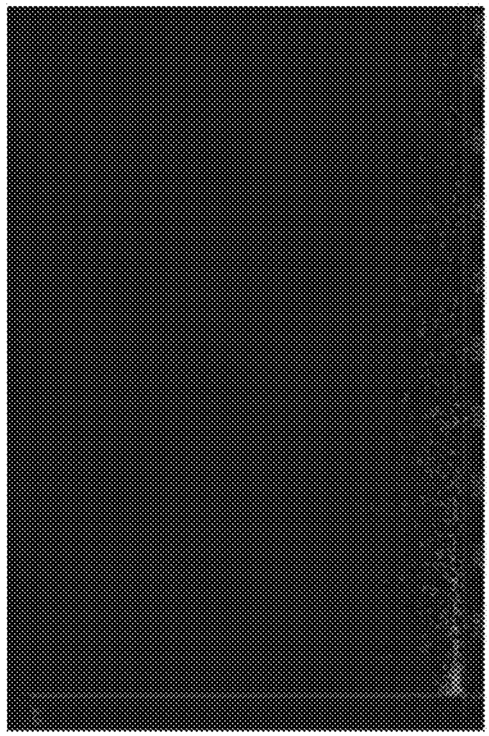
FIG. 11C

FIG. 12B
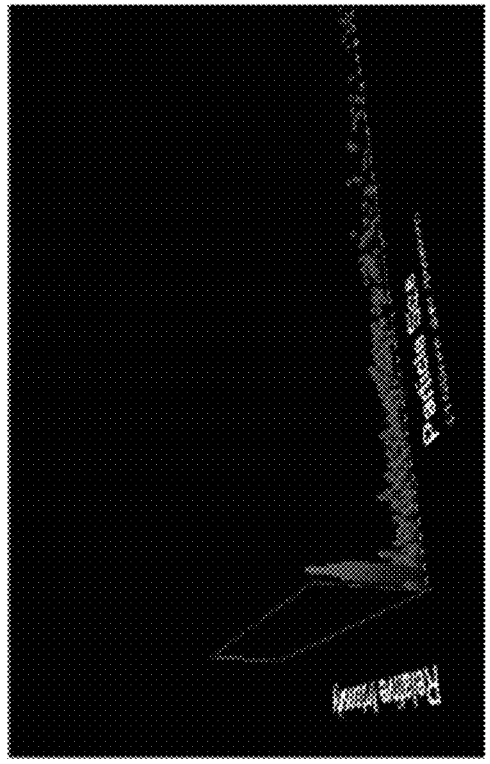
FIG. 12D
FIG. 12A
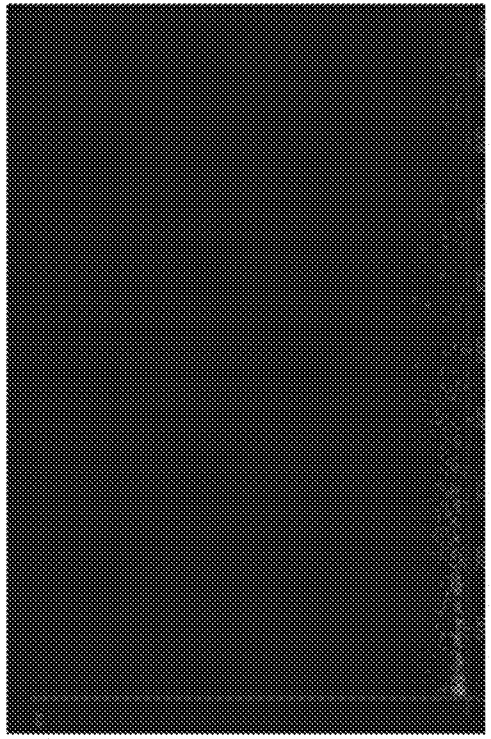
FIG. 12C

FIG. 13A

| PBS PREP | | | Light Scatter | | | Fluorescence | | [Protein] (ug/mL) | Ratio particles/protein (/ug) (x10^8) |
|---|---|---|---|---|---|---|---|---|---|
| IHMRI ID | Munster ID | Parameter | Average | SD | Parameter | Average | SD | | |
| E29 | 150 | # particles (x 10^10 /mL) | 3 | 0.4 | # particles (x 10^8 /mL) | 0.8 | 0.1 | 15.8 | 19.0 |
| | | Mode size (nm) | 125 | 8.1 | Mode size (nm) | 21.3 | 9.8 | | |
| | | Polydispersity index | 3.5 | 0.1 | Polydispersity index | 13.5 | 4.6 | | |
| E30 | 151 | # particles (x 10^10 /mL) | 3.6 | 0.4 | # particles (x 10^8 /mL) | 1.5 | 0.3 | 13.8 | 28.1 |
| | | Mode size (nm) | 145 | 29.1 | Mode size (nm) | 14.3 | 2.5 | | |
| | | Polydispersity index | 3.5 | 0.2 | Polydispersity index | 16.1 | 4.3 | | |
| E31 | 8-CO (2) | # particles (x 10^10 /mL) | 3.5 | 0.2 | # particles (x 10^8 /mL) | 1.8 | 0.1 | 12 | 20.8 |
| | | Mode size (nm) | 89 | 2.6 | Mode size (nm) | 23.0 | 8.2 | | |
| | | Polydispersity index | 6.1 | 0.2 | Polydispersity index | 7.7 | 0.5 | | |
| E32 | 9-CO (3) | # particles (x 10^10 /mL) | 2.1 | 0.2 | # particles (x 10^8 /mL) | 1.4 | 0.1 | 7.7 | 27.3 |
| | | Mode size (nm) | 44.3 | 14 | Mode size (nm) | 262.7 | 55.4 | | |
| | | Polydispersity index | 4.8 | 0.3 | Polydispersity index | 5.6 | 0.2 | | |
| E33 | 11-WH (1) | # particles (x 10^10 /mL) | 1.8 | 0.1 | # particles (x 10^8 /mL) | 0.8 | 0.1 | 5.3 | 34.0 |
| | | Mode size (nm) | 75.7 | 12.7 | Mode size (nm) | 268.0 | 73.8 | | |
| | | Polydispersity index | 5.4 | 0.3 | Polydispersity index | 4.3 | 0.6 | | |
| E34 | 12-WH (2) | # particles (x 10^10 /mL) | 1.1 | 0.3 | # particles (x 10^8 /mL) | 0.3 | 0.1 | 3.3 | 33.3 |
| | | Mode size (nm) | 75 | 4 | Mode size (nm) | 15.0 | 3.6 | | |
| | | Polydispersity index | 5.6 | 0.3 | Polydispersity index | 5.7 | 0.5 | | |
| E35 | 32-BOTHER (1) | # particles (x 10^10 /mL) | 2.1 | 6 | # particles (x 10^8 /mL) | 1.6 | 0.2 | 5.9 | 35.6 |
| | | Mode size (nm) | 73.7 | 18.6 | Mode size (nm) | 177.2 | 32.9 | | |
| | | Polydispersity index | 5.5 | 0.3 | Polydispersity index | 5.3 | 0.8 | | |
| E36 | 6-KW Lo | # particles (x 10^10 /mL) | 1.7 | 0.3 | # particles (x 10^8 /mL) | 0.6 | 0.3 | 4.3 | 39.5 |
| | | Mode size (nm) | 96.3 | 8.5 | Mode size (nm) | 13.0 | 5.6 | | |
| | | Polydispersity index | 4.6 | 0.4 | Polydispersity index | 9.8 | 3.2 | | |
| E37 | 24-M 2 | # particles (x 10^10 /mL) | 1.2 | 0.1 | # particles (x 10^8 /mL) | 0.8 | 0.1 | 4.1 | 29.3 |
| | | Mode size (nm) | 88.7 | 10.2 | Mode size (nm) | 74.7 | 103.6 | | |
| | | Polydispersity index | 5.8 | 0.9 | Polydispersity index | 13.1 | 6.4 | | |
| E38 | 27-AM Lo | # particles (x 10^10 /mL) | 1.1 | 0.2 | # particles (x 10^8 /mL) | 1.2 | 0.2 | 3.9 | 28.2 |
| | | Mode size (nm) | 105 | 10.6 | Mode size (nm) | 139.3 | 92.9 | | |
| | | Polydispersity index | 4.9 | 0.3 | Polydispersity index | 6.0 | 0.6 | | |
| E39 | 36-VS Lo 2 | # particles (x 10^10 /mL) | 2.6 | 0.2 | # particles (x 10^8 /mL) | 0.6 | 0.2 | 3.6 | 30.7 |
| | | Mode size (nm) | 91.7 | 45.7 | Mode size (nm) | 95.0 | 7.1 | | |
| | | Polydispersity index | 3.9 | 0.3 | Polydispersity index | 5.3 | 0.2 | | |
| E40 | 7-CO Red Tube | # particles (x 10^10 /mL) | 2.4 | 0.2 | # particles (x 10^8 /mL) | 1.2 | 0.4 | 20.1 | 11.9 |
| | | Mode size (nm) | 81.7 | 4.5 | Mode size (nm) | 17.0 | 5.6 | | |
| | | Polydispersity index | 5.6 | 0.4 | Polydispersity index | 12.9 | 4.2 | | |
| E41 | 19-MG 1 | # particles (x 10^10 /mL) | 1.5 | 0.2 | # particles (x 10^8 /mL) | 1.1 | 0.3 | 5.1 | 29.4 |
| | | Mode size (nm) | 102 | 19.1 | Mode size (nm) | 102.0 | 76.2 | | |
| | | Polydispersity index | 6.2 | 0.1 | Polydispersity index | 3.4 | 3.2 | | |
| E42 | 20-MG 2 | # particles (x 10^10 /mL) | 1.6 | 0.3 | # particles (x 10^8 /mL) | 1.0 | 0.4 | 4.1 | 39.0 |
| | | Mode size (nm) | 72.7 | 7.5 | Mode size (nm) | 156.7 | 129.3 | | |
| | | Polydispersity index | 5.2 | 0.7 | Polydispersity index | 10.0 | 8.6 | | |

FIG. 13B

| Water PREP | | Light Scatter | | | Fluorescence | | | [Protein] (ug/mL) | Ratio particles/protein (/ug) (x10^8) |
|---|---|---|---|---|---|---|---|---|---|
| DHMRI ID | Munster ID | Parameter | Average | SD | Parameter | Average | SD | | |
| E43 | 19MG-1 | # particles (x 10^10 /mL) | 7.6 | 1.2 | # particles (x 10^8 /mL) | 0.8 | 0.3 | 218.9 | 3.5 |
| | | Mode size (nm) | 72.3 | 13.1 | Mode size (nm) | 15.7 | 3.8 | | |
| | | Polydispersity index | 3.8 | 0.6 | Polydispersity index | 10.1 | 3.7 | | |
| E44 | 32-Rother (1) | # particles (x 10^10 /mL) | 8.6 | 0.8 | # particles (x 10^8 /mL) | 1.1 | 0.3 | 346.8 | 2.5 |
| | | Mode size (nm) | 101.3 | 16.8 | Mode size (nm) | 15.7 | 4.7 | | |
| | | Polydispersity index | 5.3 | 0.5 | Polydispersity index | 16.2 | 3.0 | | |
| E45 | 27-AM i.o | # particles (x 10^10 /mL) | 9.5 | 0.1 | # particles (x 10^8 /mL) | 0.6 | 0.4 | 270.6 | 3.3 |
| | | Mode size (nm) | 62.3 | 6.8 | Mode size (nm) | 36.7 | 34.4 | | |
| | | Polydispersity index | 5.1 | 0.1 | Polydispersity index | 7.5 | 3.2 | | |
| E46 | 36-VS i.o 2 | # particles (x 10^10 /mL) | 8.5 | 1.7 | # particles (x 10^8 /mL) | 0.6 | 0.3 | 258.3 | 3.3 |
| | | Mode size (nm) | 89.7 | 5.5 | Mode size (nm) | 23.0 | 5.6 | | |
| | | Polydispersity index | 5.4 | 0 | Polydispersity index | 8.1 | 5.3 | | |
| E53 | 8-CO (2) | # particles (x 10^10 /mL) | 10.3 | 0.3 | # particles (x 10^8 /mL) | 1.2 | 0.2 | 328.5 | 3.1 |
| | | Mode size (nm) | 73.7 | 10 | Mode size (nm) | 20.7 | 3.1 | | |
| | | Polydispersity index | 6.1 | 0.5 | Polydispersity index | 16.5 | 1.9 | | |
| E54 | 9-CO (3) | # particles (x 10^10 /mL) | 8.8 | 0.2 | # particles (x 10^8 /mL) | 1.2 | 0.4 | 277.9 | 3.2 |
| | | Mode size (nm) | 65 | 8.7 | Mode size (nm) | 20.7 | 4.0 | | |
| | | Polydispersity index | 6.1 | 0.3 | Polydispersity index | 14.9 | 4.4 | | |

5-ALA FOR DETECTION OF BRAIN TUMORS

CROSS REFERENCE TO RELATED APPLICATIONS

This application is a Continuation application of U.S. application Ser. No. 15/277,982, filed Sep. 27, 2016, which is a Divisional application of U.S. application Ser. No. 13/838,895, filed Mar. 15, 2013, now U.S. Pat. No. 9,493,810, issued Nov. 15, 2016, which claims priority to and the benefit of U.S. Provisional Application No. 61/656,945, filed Jun. 7, 2012, each of which is herein incorporated by reference in its entirety.

FIELD OF THE INVENTION

The present disclosure relates to methods for detecting brain tumors and assessing the presence and recurrence of such tumors.

BACKGROUND

The most common form of the cancer originating in the brain is the most aggressive and advanced Stage IV variety called glioblastoma. Lower grade gliomas often progress to later become Stage IV GBMs. Currently, the differentiation of disease recurrence during the standard management of this life-threatening disease is very complex and difficult to distinguish from tumor necrosis following radiation therapy, making treatment and definition of risk very complex and inaccurate The current standard treatment regimen for GBM includes surgical resection, external beam radiation, and oral chemotherapy. However, life expectancy is typically only 12-16 months due to the challenges to treatment including the tentacle-like protrusions of the tumor which are difficult to excise and the limited drug access due to the blood-brain barrier. Given the limited effectiveness of treatment and likelihood of recurrence, it is important to closely monitor patients following treatment. At present MRI imaging is unable to adequately discriminate between radio-necrosis due to radiation treatment and recurrence of the solid brain tumor. As such practitioners are forced to empirically assess patient progress by methods such as MRI or are required to use tumor biopsies for advanced PET and SPECT imaging studies. These processes have significant impact on patient welfare and cost of care.

Standard treatment regimens and the challenges for treatment of other WHO Grade III and Grade IV tumors are similar.

Gliolan, of which 5-ALA is an active ingredient, is approved in Europe for use as a reagent to enable the differential visualization of tumor tissue vs. normal brain tissue under fluorescence and permit more complete resection rates by the neurosurgeon. High-grade brain tumors (WHO-grade III and IV, e.g., GBM, gliosarcoma, anaplastic astrocytoma) metabolize 5-ALA to fluorescent porphyrins at rates higher then normal brain tissue and low-grade brain tumors (WHO grade I and II, e.g., medulloblastoma, oligdendroglioma) and therefore have increased fluorescence. However, it is unknown whether 5-ALA signal can be detected non-invasively.

Accordingly, there remains a need for simple, non-invasive methods to detect WHO Grade III and IV brain tumors and assess the presence and recurrence of such tumors in a variety of subjects.

In addition, there remains a general need for simple, non-invasive methods to detect and assess all types of solid tumors and to detect response to treatment or breakthrough resulting in disease recurrence.

BRIEF SUMMARY

In order to meet the above needs, the present disclosure provides the methods described herein.

The present disclosure describes methods for detecting WHO grade III and grade IV brain tumors and assessing the presence and recurrence of such tumors by quantitating enzymatic biomarkers or the end products in the metabolism of aminolevulenic acid metabolism associated with microparticles shed from these tumors and isolated from bodily fluids following the administration of a pharmaceutical composition having 5-aminolevulinic acid (5-ALA) as an active ingredient and detecting 5-ALA associated with brain-derived microparticles.

In one aspect, the disclosure provides methods for detecting a WHO grade III or grade IV brain tumor, wherein the method includes the steps of administering a pharmaceutical composition including 5-aminolevulinic acid (5-ALA) to a subject; and detecting the level of conversion of 5-ALA to protoporphyrin IX (PPIX) in the tumor by means of measuring the quantity of shed microparticles and detecting the presence of PPIX associated with brain-derived microparticles in a biological sample from the subject, thereby detecting the presence or recurrence of WHO grade III or grade IV brain tumor.

When practicing the above methods, the level of conversion of 5-ALA to PPIX can be detected by measuring fluorescence, measuring the level of a metabolite along the 5-ALA to PPIX conversion pathway, or measuring the level of a converting enzyme such as coproporphyrinogen oxidase (CPDX).

In some embodiments of the above methods, the methods include a step of isolating the brain-derived microparticles from the biological sample prior to detecting 5-ALA associated with the brain-derived microparticles.

In another aspect, the present disclosure describes methods for assessing the recurrence of WHO grade III and grade IV brain tumors, wherein the method includes the steps of administering a pharmaceutical composition comprising 5-aminolevulinic acid (5-ALA) to a subject; and assessing the recurrence of WHO grade III and grade IV brain tumors by detecting 5-ALA associated with brain-derived microparticles in a biological sample from the subject. The recurrence of WHO grade III and grade IV brain tumors may be assessed by detecting the quantity of 5-ALA associated with brain-derived microparticles. In some embodiments, the methods detect recurrence by detecting the level of conversion of 5-ALA to PPIX using the methods described for the preceding aspect.

In certain embodiments of the above aspects, the subject was previously treated for a brain tumor, in particular, a WHO grade III or grade IV brain tumor. The treated tumor may be anaplastic astrocytoma, glioblastoma, anaplastic oligodendroglioma, anaplastic ependymoma, anaplastic oligoastrocytoma, polar spongioblastoma, astroblastoma, or gliomatosis cerebri.

In yet another aspect, the present disclosure provides methods for detecting a solid tumor, wherein the method includes the steps of administering a cancer drug which preferentially localizes to a solid tumor to a subject, wherein the drug is converted into metabolites; and detecting a metabolite or a converting enzyme associated with solid tumor-derived microparticles in a biological sample from the subject, thereby detecting the solid tumor.

In still yet another aspect, the present disclosure provides methods for measuring the level of a cancer drug targeted to a solid tumor, wherein the method includes the steps of administering a cancer drug which preferentially localizes to a solid tumor to a subject, wherein the drug is converted into metabolites; detecting the level of a metabolite associated with solid tumor-derived microparticles in a biological sample from the subject, and determining the level of the cancer drug or a converting enzyme in the solid tumor based on the level of metabolites.

Preferred solid tumors for the above preceding aspects include ovarian, breast, pancreatic, prostate, lung, colorectal, renal and bladder.

In certain embodiments of all of the above aspects, the biological sample is whole blood, serum, plasma, or cerebrospinal fluid. In other embodiments, the biological sample is serum, urine, tears, milk, lymph fluid, synovial fluid, bronchoalveolar lavage, amniotic fluid, saliva, ocular fluid, ascites, or respiratory droplets.

The pharmaceutical composition used in certain embodiments of all of the above aspects can be any composition including 5-ALA, but is typically Gliolan™. The pharmaceutical composition can be administered orally, intravenously, intrathecally or intraumorally. In preferred embodiments, the pharmaceutical composition includes 5-ALA at a concentration of 20 mg/kg. The composition may be administered for three, four, or five hours.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows microparticle sample size distribution and concentration. FIG. 3B shows a sample video frame from the NTA analysis with red dots representing tracked particles. FIG. 3C shows microparticle sample size and relative intensity. FIG. 3D shows microparticle sample size and relative intensity in a 3D plot.

FIG. 4A shows microparticle sample size distribution and concentration. FIG. 4B shows a sample video frame from the NTA analysis with red dots representing tracked particles. FIG. 4C shows microparticle sample size and relative intensity. FIG. 4D shows microparticle sample size and relative intensity in a 3D plot with lower values and higher values represented in blue and red, respectively.

FIGS. 5A-5D relate to a PBS-processed patient sample analyzed by NTA in fluorescence mode, with the sample rendering a clear distribution of large microparticles with few small microparticles and a low polydispersity index. FIG. 5A shows microparticle sample size distribution and concentration. FIG. 5B shows a sample video frame from the NTA analysis with red dots representing tracked particles. FIG. 5C shows microparticle sample size and relative intensity. FIG. 5D shows microparticle sample size and relative intensity in a 3D plot with lower values and higher values represented in blue and red, respectively.

FIG. 6A shows microparticle sample size distribution and concentration. FIG. 6B shows a sample video frame from the NTA analysis with light blue dots representing fluorescently tracked particles. FIG. 6C shows microparticle sample size and relative intensity. FIG. 6D shows microparticle sample size and relative intensity in a 3D plot with lower values and higher values represented in blue and red, respectively.

FIG. 7A shows microparticle sample size distribution and concentration. FIG. 7B shows a sample video frame from the NTA analysis with light blue dots representing fluorescently tracked particles. FIG. 7C shows microparticle sample size and relative intensity. FIG. 7D shows microparticle sample size and relative intensity in a 3D plot with lower values and higher values represented in blue and red, respectively.

FIG. 8A shows microparticle sample size distribution and concentration. FIG. 8B shows a sample video frame from the NTA analysis with light blue dots representing fluorescently tracked particles. FIG. 8C shows microparticle sample size and relative intensity. FIG. 8D shows microparticle sample size and relative intensity in a 3D plot with lower values and higher values represented in blue and red, respectively.

FIG. 9A shows microparticle sample size distribution and concentration. FIG. 9B shows a sample video frame from the NTA analysis with light blue dots representing fluorescently tracked particles. FIG. 9C shows microparticle sample size and relative intensity. FIG. 9D shows microparticle sample size and relative intensity in a 3D plot with lower values and higher values represented in blue and red, respectively.

FIGS. 10A-10D relate to a water-processed patient sample analyzed by NTA in fluorescence mode, with the sample rendering a large number of small microparticles with no obvious distribution of large microparticles and a high polydispersity index. FIG. 10A shows microparticle sample size distribution and concentration. FIG. 10B shows a sample video frame from the NTA analysis with light blue dots representing fluorescently tracked particles. FIG. 10C shows microparticle sample size and relative intensity. FIG. 10D shows microparticle sample size and relative intensity in a 3D plot with lower values and higher values represented in blue and red, respectively.

FIGS. 11A-11D relate to a water-processed patient sample analyzed by NTA in fluorescence mode, with the sample rendering a large number of small microparticles with no obvious distribution of large microparticles and a very high polydispersity index. FIG. 11A shows microparticle sample size distribution and concentration. FIG. 11B shows a sample video frame from the NTA analysis with red dots representing tracked particles. FIG. 11C shows microparticle sample size and relative intensity. FIG. 11D shows microparticle sample size and relative intensity in a 3D plot with lower values and higher values represented in blue and red, respectively.

FIGS. 12A-12D relate to a water-processed patient sample analyzed by NTA in fluorescence mode, with the sample rendering a large number of small microparticles with no obvious distribution of large microparticles and a very high polydispersity index. FIG. 12A shows microparticle sample size distribution and concentration. FIG. 12B shows a sample video frame from the NTA analysis with red dots representing tracked particles. FIG. 12C shows microparticle sample size and relative intensity. FIG. 12D shows microparticle sample size and relative intensity in a 3D plot with lower values and higher values represented in blue and red, respectively.

FIGS. 13A-13B illustrate a summary of the microparticle quantitation results following size-exclusion chromatography in water vs PBS via light scattering and fluorescence NTA. FIG. 13A illustrates the results from the PBS preparation. FIG. 13B illustrates the results from the water preparation.

DETAILED DESCRIPTION OF THE PREFERRED EMBODIMENTS

Definitions

Figure 1B:
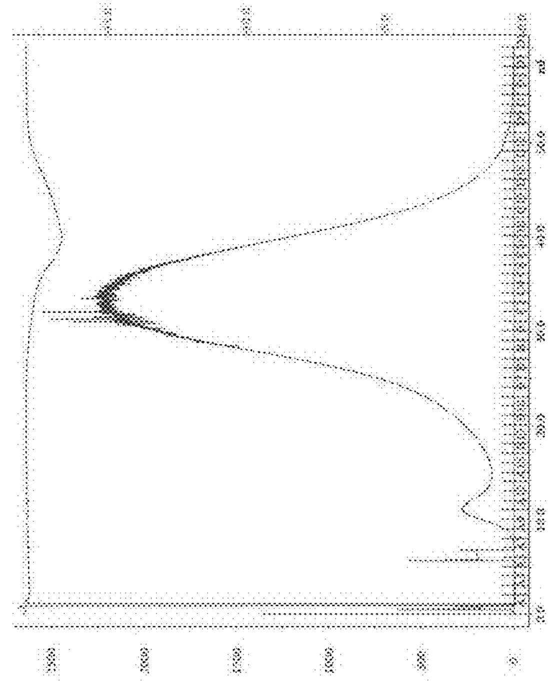
FIG. 1B shows size exclusion chromatography (left axis, blue trace, absorbance at 280 nm) and conductivity measurements (right axis, brown trace) of control serum in 100% PBS.

The term "5-ALA" as used herein refers to 5-aminolevulinic acid.

The term "PPIX" as used herein refers to protoporphyrin IX.

The term "microparticle" as used herein refers to any small vesicles released from any cell type. Microparticles include, for example, exosomes and microvesicles.

The term "WHO Grade III or IV" as used herein refers to tumors that have been in actuality graded as meeting the standards for WHO Grade III or IV, or that would have been graded as such if they had been evaluated under the WHO standards.

Overview

The present disclosure relates to methods for detecting a solid tumor by administering a cancer drug used for fluorescent guided visualization of tumor cells which preferentially localizes to a solid tumor, and detecting drug metabolites or converting enzymes associated with solid tumor-derived microparticles in a biological sample from the subject.

More particularly, the present disclosure relates to methods to detect a WHO grade III or grade IV brain tumor or to detect recurrence of such tumors by administering a pharmaceutical composition having 5-aminolevulinic acid (5-ALA) as an active ingredient to a subject, and detecting the level of the conversion of 5-ALA to PPIX in a biological sample from the subject.

The present disclosure also relates to methods for detecting a solid tumor by administering high dosages of an endogenous amino acid used as an adjunct to fluorescent-guided surgery for solid tumors and detecting metabolites or converting enzymes associated with solid tumor-derived microparticles in a biological sample from the subject.

The present disclosure also relates to methods for measuring the level of a cancer drug targeted to a solid tumor by administering a cancer drug which preferentially localizes to a solid tumor, detecting the level of metabolites associated with solid tumor-derived microparticles in a biological sample from the subject; and determining the levels of a cancer drug in the solid tumor based on the level of metabolites.

The present disclosure is based at least in part on the understanding that PPIX, the porphyrin metabolite of 5-ALA, selectively accumulates in brain tumor cells and the novel discovery that PPIX is found in microparticles shed from WHO grade III and grade IV brain tumors at concentrations in equilibrium with the intracellular concentrations of PPIX.

Methods for Detecting Solid Tumors

The methods described herein detect WHO grade III and grade IV brain tumors, such as anaplastic astrocytoma, glioblastoma multiforme, anaplastic oligodendroglioma, anaplastic ependymoma, anaplastic oligoastrocytoma, polar spongioblastoma, astroblastoma, or gliomatosis cerebri.

The pharmaceutical composition having 5-ALA as an active ingredient can be used to detect WHO grade III and grade IV brain tumors in any subject for whom the benefits of detection of such tumors using this method outweigh any potential deleterious effects of administration of the pharmaceutical composition. In some embodiments, this includes subjects suffering from symptoms indicative of the brain tumor where other non-invasive means for detection are not suitable or where detection using 5-ALA has greater sensitivity than other methods.

In certain embodiments, the pharmaceutical composition is administered to those subjects were previously treated for least one brain tumor, in some instances a WHO grade III or grade IV tumor. These subjects may have previously treated with surgery, radiotherapy, chemotherapy, a combination thereof, or any other suitable treatment. In the specific instances where the method is used on subjects who were previously treated for a grade III or grade IV tumor, the method is used to detect recurrence of the tumor.

The methods herein can also be also to detect other types of brain tumors, as well as other solid tumors, of any WHO grade, which metabolize 5-ALA at a higher rate than tissue from which it needs to differentiated, e.g., normal tissue. In particular, this method can be used for highly proliferative tumors including, but not limited to ovarian, breast, pancreatic, prostate, lung, colorectal, renal and bladder tumors. It should be understood that although some of the embodiments herein are described only with respect to brain tumors, these embodiments are also present with respect to detection of other solid tumors.

Other Methods

Methods herein can also be used to assess the recurrence of solid tumors, volume of solid tumors, or the extent of solid tumor burden by detecting the level of conversion of 5-ALA to PPIX associated with tumor-derived microvesicles using the methods described herein.

Pharmaceutical Compositions Having 5-Aminolevulinic Acid as an Active Ingredient The pharmaceutical compositions disclosed herein have 5-aminolevulinic acid (5-ALA) as an active ingredient. Exemplary preferred 5-ALA concentrations in the pharmaceutical composition include 1 mg/mL, 3 mg/mL, 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, and 60 mg/mL in powder form. The 5-ALA may be in any form which is suitable for administration to a subject, such as free powder, powder reconstituted in liquid, tablet, or capsule.

In some embodiments, 5-ALA is the only active ingredient in the pharmaceutical compositions disclosed herein. In other embodiments, the compositions contain other active ingredients which either enhances 5-ALA's ability to localize specifically in solid tumor cells, or themselves localize specifically in solid tumor cells.

In a particularly preferred embodiment, the pharmaceutical composition having 5-aminolevulinic acid as an active ingredient is Gliolan™, where 5-ALA is present at a concentration of 30 mg/mL in powder.

Administration of the Pharmaceutical Composition Having 5-Aminolevulinic Acid as an Active Ingredient The pharmaceutical composition may be administered to the subject at any dosage which does not have significant side effects and which can be metabolized by the subject such that the cytosol of the tumor is sufficiently loaded after a time suitable for the methods described herein. Exemplary dosages include 5-ALA at dosages of 1 mg/mL, 3 mg/mL, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, and 60 mg/kg.

Due to convenience, oral administration of the pharmaceutical composition is preferred. However, the pharmaceutical composition may also be formulated to be administered via other routes, such as intravenously, intrathecally, intratumorally or directly into the cystic space intraoperatively as a lavage or infusion.

The pharmaceutical composition is administered sufficiently before the desired time for detection of the microparticle-associated 5-ALA such that the cytosol of the tumor is loaded with 5-ALA and begins to release microparticles. Preferably, the pharmaceutical composition is administered early enough that the 5-ALA content in the microparticles is in equilibrium with the 5-ALA in the cytosol of the tumor. For example, the pharmaceutical composition can be administered 1 hour, 2 hours, 3 hours, 4 hours, 5 hours, 6 hours, 7 hours, 8 hours, 9 hours, 10 hours, 24 hours, or 48 hours prior to detection of the microparticle-associated 5-ALA. Most preferably, the 5-ALA is administered between two to four hours before the detection event, most preferably, four hours prior.

Biological Samples

The biological samples to be used in the methods described herein include any biological sample which contains solid tumor-derived microparticles in sufficient quantities to permit detection of 5-ALA. The sample is preferably whole blood, serum or plasma. In some embodiments, the biological sample is serum, urine, tears, milk, lymph fluid, synovial fluid, bronchoalveolar lavage, amniotic fluid, saliva, ocular fluid, ascites, or respiratory droplets.

Detecting the Level of Conversion of 5-Aminolevulinic Acid to PPIX Associated with Solid Tumor-Derived Microparticles The level of conversion of 5-aminolevulinic acid to PPIX associated with solid tumor-derived microparticles can be detected using any methods known to those of skill in the art.

Microparticle Isolation

An initial step in these methods may include isolation of microparticles derived from all types of tissues using standard methods known to those of skill in the art including but not limited to ultracentrifugation, sucrose gradient, affinity purification, filtration, gel filtration or affinity capture resulting in isolation of microparticles with specific identity markers (e.g., annexin).

The next step in these methods may be isolating a population of tissue-specific microparticles.

If brain-derived microparticles are needed and the biological sample is one only expected to contain brain-derived microparticles, then no specific step is required to isolate or identify those specifically derived from brain. However, since 5-ALA associates with tissues other than brain, if the biological sample is one which may contain microparticles derived from non-brain tissues, the method should include a step which either isolates or identifies brain-derived microparticles. Exemplary brain-specific tumor markers include EGFRviii, Tenascin-C. Alternative methods include using other antibody-antigens found on other cell types to eliminate other tissues as sources of the microparticles. For example, RGD integrins (alpha V beta 3) and glycophorin A monoclonals can be used to distinguish between microparticles originating from myeloid cells versus brain versus endothelial cells. For example, microparticles which have glycophorin are derived from bone marrow.

Detection of Conversion of 5-ALA to PPIX

After isolation of tumor-derived microparticles, the level of conversion of 5-ALA to PPIX associated with these microparticles can be measured by several methods. An exemplary method is detection of the PPIX into which 5-ALA metabolizes. Then can be performed by detecting fluorescence of the PPIX. When excited with blue light (wavelength 400-410 nm), PPIX emits a red-violet light. Fluorescence may be detected in the context of nanoparticle tracking analysis, for example, using the NTA analysis procedure (Nanosight Ltd, Wiltshire, UK), which directly measures and quantitates total number of microparticles.

Another method is detection of the 5-ALA to PPIX converting enzymes including, but not limited to protoporphyrinogen oxidase, ALA dehydratase, PBG deaminase, uroporphyrinogen III synthase, uroporphyrinogen decarboxylase, and coproporphyrinogen III oxidase (CPDX). Yet another method is detection of key metabolites or intermediates in the conversion pathway including, but not limited to, porphobilinogen (PBG), hydroxymethylbilane, uroporphyrinogen III, coprophyrinogen III, or protoporphyrinogen.

EXAMPLES

Example 1: Detection and Characterization of Blood-Derived Microparticles from 5-Ala Treated GBM Patients This Example demonstrates detection of a small molecule drug following oral dosing. The drug can be uptaken by tumor cells, enzymatically modified, and shed back into circulating microparticles within hours of dosing. Further-more, the enzymatic modification of the small molecule drug in the tumor cells was detectable by fluorescence from blood-derived microparticles.

The purpose of this study was to (i) isolate nanometer-diameter microparticles from the serum of glioblastoma (GBM) patients that have taken Gliolan™ PO, (ii) quantify their number using two different isolation methods ($ddH_2O$ and PBS-based chromatography) and (iii) assess whether or not these microparticles contain detectable levels of endogenous fluorescence when excited with a UV laser.

Gliolan® (5-aminolevulinic acid hydrochloride) is currently approved in Europe for the intraoperative visualization of malignant tissue during glioma surgery (WHO grade III and IV). The agent is currently being studied as an adjunct to fluorescent-guided surgery to maximize tumor resection. The present study was undertaken to define if tumors loaded with Gliolan® could shed circulating microparticles containing 5-ALA derived fluorophore as a novel tool to endogenously label, track and quantify tumor derived microparticles.

Serum samples from GBM patients (n=19, oral tumor specificity, enhanced surgical outcome) undergoing surgery were collected prior to, and at different time points up to 48 hours following oral dosing with Gliolan® (20 mg/kg). Microparticles were isolated by gel filtration and characterized using Nanoparticle Tracking Analysis (NTA) and BCA for microparticle size/number and protein content. Endogenous fluorescence from the microparticles was assessed using NTA in the fluorescence detection mode ($\lambda ex=405$ nm, $\lambda em>430$ nm). Results suggest that microparticles (mode diameter of 50-100 nm) are present at a concentration of ~10^11 particles/mL of serum (protein content=283.5+47 μg/ml of sera). Multiple microparticle phenotypes based upon size (~20 nm to ~200 nm) were observed under fluorescence mode implying capture of cytosolic fluorophore during biogenesis of at least two major populations of shed microparticles. Microparticles from GBM patients administered Gliolan® contain an fluorescent species that is observed in a small (~0.1%) fraction of the total number of microparticles after dosing suggesting that cellular cytosol may circulate with shed microparticles. These results are quantifiable from 4-48 hours.

This is the first evidence that a small molecule drug following oral dosage can be uptaken by tumor cells, enzymatically modified and shed back into circulating microparticles within hours of dosing. This direct measure of tumor function affords multiple therapeutic and drug development implications for this novel "liquid biopsy" procedure.

Brief Materials and Methods

Microparticle Isolation

Frozen serum samples were received from GBM patients undergoing surgery at two clinical centers. These serum samples were collected immediately prior to, and at different time points following, PO dosing with Gliolan™ (5-aminolevulinic acid, 5-ALA).

Microparticles were isolated from control ('healthy' AB serum, Sigma Aldrich, St. Louis, Mo.) and from patient serum or plasma samples using size-exclusion chromatography with 2% agarose (agarose 2B, ABT, www.abtbeads.com) as the solid phase and $ddH_2O$ or PBS, pH 7.4 as the mobile phase. The column was packed in a Bio-Rad Econo column (2.5 cm ID×10 cm) with 100 mL of 40% v/v agarose slurry in $ddH_2O$, resulting in a column of ~40 mL final packed bed volume and equilibrated overnight at 4° C. The column was washed with 300 mL of the mobile phase to equilibrate the column on the day of experimentation. The load sample to bed volume varied from 1-2.5% v/v, well within the guidance of the manufacturer for SEC (<5% v/v).

Serum, plasma and microparticle samples were processed as much as practically possible under dark ambient conditions. Microparticles were collected and stored in amber Eppendorf tubes. A protein standard and Blue Dextran mix was used to define the void (excluded) volume of the column (~10 ml—where microparticles would be predicted to elute) and of the retained (included) volume of the column (~40 mL).

Samples were processed using a GE AKTA Purifier 10 system (GE Healthcare, Piscataway, N.J.) with a Frac 950 fraction collector at room temperature with a diluent run at the rate of 2 mLs/min while monitoring sample $A_{280}$ and sample conductivity. Using a flow rate of 2 mL/min and a 30-second collection periodicity, 1 mL elution samples were obtained.

Serum from either study samples or human healthy controls (AB serum, Sigma Aldrich) yielded two partially resolved peaks (#1 and #2) with retention volumes of ~10 mL and ~40 mL when monitored by $A_{280}$. Serum from multiple donor sites yielded similar elution profiles. The majority of the conductivity in the sample was associated with the latter of the two peaks (elution volume ~40 mL) as might be expected for ions, charged amino acids/peptides and other low molecular weight species when eluted from a 2% agarose size exclusion column. This parameter was used to demark the beginning of the second peak (peak #2).

Given their high molecular weight, microparticles elute in the void (excluded) volume of the agarose column (peak #1). The first 7×1 mL fractions associated with peak #1 absorbance $A_{280}$ were collected, pooled, separated into 7×1-mL aliquots for subsequent processing and stored at −80° C. One milliliter fractions from peak #1 for each sample in the study set were analyzed for total protein and microparticle content (see below).

Microparticle Protein Content

Total protein concentration in the microparticle preparation was determined using a Thermo Scientific Micro bicinchoninic acid (BCA) Protein Assay according to the manufacturer's instructions using BSA to generate the standard curve.

Microparticle Content and Size Distribution

Microparticles—those with a mean hydrodynamic diameter of between 50-500 nm—were quantified using the Nanoparticle Tracking Analysis (NTA) method (Nanosight, LM 10 system, NanoSight Ltd. Wiltshire, UK). This stochastic single particle detection method is based on light scattering from individual particles using the Stokes-Einstein relationship to measure the average (time-averaged, field of view) number of particles and their predicted hydrodynamic diameter. Further details are available at www.nanosight.com and in Dragovic et al., (2011) and references therein.

The instrument was calibrated and validated with standard beads—from 50-400 nm. One hundred nm beads were run each day to calibrate the system. Standard beads (100 nm diameter) yielded experimental diameters of ~97 (±2) nm in aqueous, low viscosity (~1 cP) solutions at room temperature. Microparticles of interest are predicted to have a mean hydrodynamic diameter of 50-150 nm.

All measurements were undertaken using the manufacturer's instructions e.g. for target particles per frame, duration of data collection; PMT voltages, discrimination settings etc. (see www.nanosight.com and Dragovic et al., (2011) (Sizing and phenotyping of cellular vesicles using Nanoparticle Tracking Analysis). Nanomedicine: NBM 2011; 7:780-788, doi:10.1016/j.nano.2011.04.003) for details of the typical instrumental settings.

Over the course of a typical fluorescence read (60 seconds), only highly photostable fluorophores will be observed since the fluorescent particles, if any, are resident in the field of illumination for a considerable fraction of the total collection period. Therefore, a variant of the LM10 NTA analysis software was used which analyses data from fluorescence collected from samples moving at a slow and constant flow rate through the observation cell. Each sample was analyzed with three repeats of each analytical measurement.

Results

Microparticle Isolation

Figure 1A:
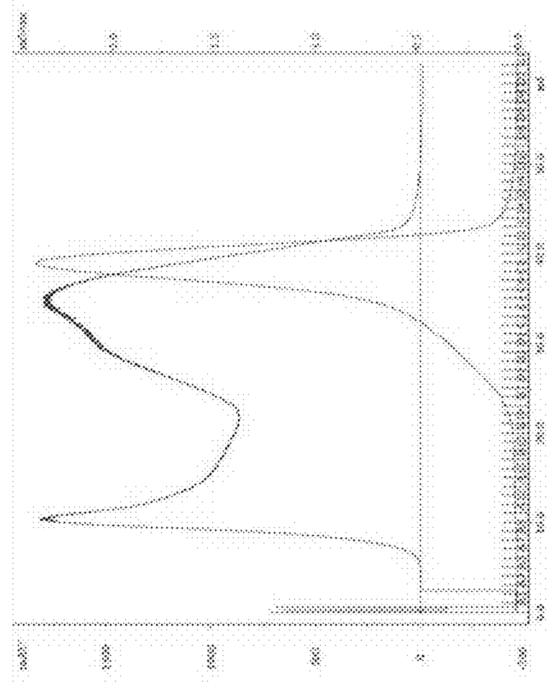
FIG. 1A shows size exclusion chromatography (left axis, blue trace, absorbance at 280 nm) and conductivity measurements (right axis, brown trace) of control serum in $ddH_2O$.

AB Control Serum:

Using $ddH_2O$ as the mobile phase, the loaded AB control serum sample led to two partially resolved $A_{280}$ nm peaks and a measurable elution of conductivity (presumably due to ions, charged peptides/metabolites etc.) which correlated almost exclusively with the second eluting peak ($V_{peak}$ ~40 mL, FIG. 1A). In contrast, no conductivity was associated with peak #1 ($V_{peak}$ ~10 mL) and which is envisaged to contain the high molecular weight microparticles of interest.

When using (100% v/v) PBS as the mobile phase, the relative $A_{280}$ peak heights for peak #1 vs. peak #2 are significantly (~90%) decreased compared those observed using $ddH_2O$ as the mobile phase (FIG. 1B). The conductivity associated with peak #2 decreased transitorily from the baseline for PBS of ~17 mS/cm and which is consistent with the peak conductivity of peak #2 being <<17 mS/cm.

Figure 2B:
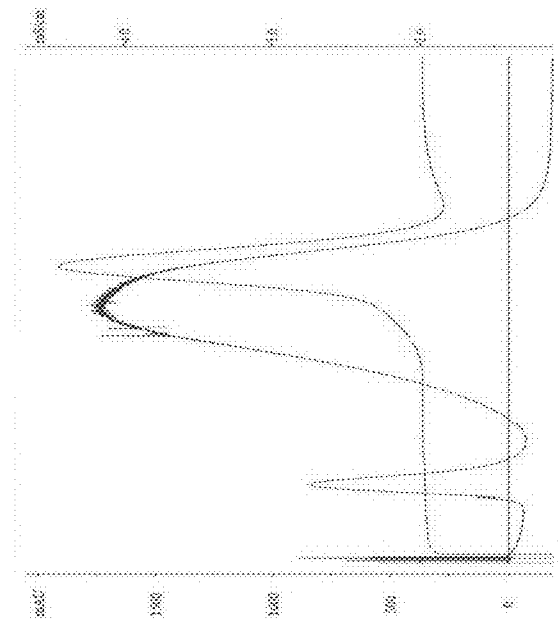
FIG. 2B shows size exclusion chromatography (left axis, blue trace, absorbance at 280 nm) and conductivity measurements (right axis, brown trace) of patient serum in 10% PBS.
Figure 2A:
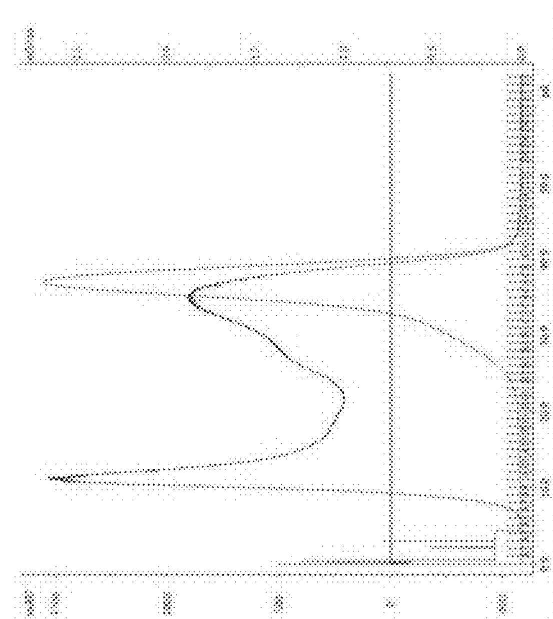
FIG. 2A shows size exclusion chromatography (left axis, blue trace, absorbance at 280 nm) and conductivity measurements (right axis, brown trace) of patient serum in $ddH_2O$.
Figure 2C:
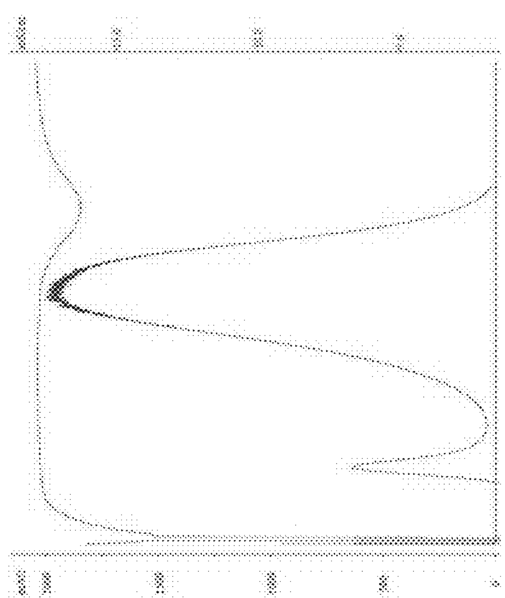
FIG. 2C shows size exclusion chromatography (left axis, blue trace, absorbance at 280 nm) and conductivity measurements (right axis, brown trace) of patient serum in 100% PBS FIGS. 3A-3D relate to a typical microparticle GBM patient sample analyzed by light scatter NTA.

GBM Patient Serum: A similar, although somewhat less pronounced, effect was observed using serum from clinical GBM patients (FIGS. 2A-2C). For this particular patient, the $A_{280}$ of peak #1 decreased from ~2000 mAU in $ddH_2O$ to ~1000 mAU and ~800 mAU in 10% PBS and 100% PBS respectively. Commensurately, the $A_{280}$ of peak #2 increased from ~1500 mAU, to ~1900 mAU to ~200 mAU, respectively. Again, the conductivity profile changed as predicted between conditions.

Using six patient samples, we isolated microparticles in $ddH_2O$ and in PBS as described above using 0.5 mL of serum and subsequently measured the protein concentration in one (of the seven) aliquots contained in peak #1 (as described for FIGS. 1A-1B, FIGS. 2A-2C). The results are shown in Table 1. For these 6 patients, the total protein concentration ranged from ~200-300 μg/mL in water to ~5-10 μg/mL in PBS.

TABLE 1

Microparticle protein isolation from size-exclusion chromatography of 0.5 mL serum

| | [Protein] (μg/mL) | | Ratio of [protein] |
|---|---|---|---|
| Sample ID | ddH20 | PBS | (PBS/ddH20) (×100) |
| E43/E41 | 218.9 | 5.1 | 2.3 |
| E44/E35 | 346.8 | 5.9 | 1.7 |
| E45/E38 | 270.6 | 3.9 | 1.4 |
| E46/E39 | 258.3 | 9.6 | 3.7 |
| E53/E31 | 328.5 | 12 | 3.7 |
| E54/E32 | 277.9 | 7.7 | 2.8 |
| Mean | 283.5 | 7.4 | 2.6 |
| Median | 274.3 | 6.8 | 2.6 |
| SD | 47.0 | 3.0 | 1.0 |

When comparing the two mobile phases in the isolation procedure, greater UV absorbance for both control and patient samples was observed when samples were eluted in a mobile phase of water compared to a mobile phase of 10% or, progressively, 100% v/v PBS. The total protein concentration in 1 mL (of a peak pooled 7 mL) of microparticles from GBM patients was ~200-300 μg/mL (est. 5 mg/mL in the original serum) when eluting with water and 5-10 μg/mL (est. 100-200 μg/mL in the original serum) when eluting in PBS. The molecular or supra-molecular origin of the detected protein in peak #1 (e.g 'exosomal', other high MW particulates) cannot be determined from the current data. These data represent the weighted average of the total protein from all sources of microparticles eluting in the void volume.

Microparticle Quantitation

The quantitation of microparticles from peak #1 of the chromatographic separations (see FIGS. 1A-1B, FIGS. 2A-2C), was undertaken using the NTA analysis procedure (Nanosight Ltd, Wiltshire, UK).

A typical Nanosight NTA analysis report is shown in FIGS. 3A-3D and which includes the particle/size distribution (top left), a sample video image (top right), and particle size vs. intensity (lower panes). Samples were typically diluted 1000-fold before analysis.

Effect of water and PBS on microparticle quantitation

For two microparticle samples (as referenced in FIGS. 2A-2C), the total number of microparticles was determined via NTA by light scattering when isolated under the three conditions, water, 10% PBS, and 100% PBS (Table 2).

Dilution Factor: N.B.:

The high molecular weight fraction from the 1 mL serum load was estimated to be diluted 7-10 fold during chromatography (15-20 fold for 0.5 mL load serum volume). Thus, whereas the total # particles in the pooled microparticle fractions shown in Table 2 are ~$3\times10^{11}$/mL, the estimated # particles per in the original serum is estimated to be ~2×, or $10^{12}$/mL. "LS" refers to light scatter detection mode, and "FL" refers to fluorescence detection mode.

TABLE 2

Microparticle quantitation via NTA following size-exclusion chromatography

| Mode | ID | Parameter | Water (Average) | 0.1X PBS (Average) | 1X PBS (Average) |
|---|---|---|---|---|---|
| LS | Munster 150 | # particles (×10^11/mL) | 3.8 ± 0.2 | 0.5 ± 0.1 | 0.3 ± 0 |
| | | Mode size (nm) | 68.7 ± 8.1 | 105 ± 47.3 | 129 ± 6.1 |
| | | Poly-dispersity index | 3.9 ± 0.3 | 4.1 ± 0.7 | 3.5 ± 0.1 |

TABLE 2-continued

Microparticle quantitation via NTA following size-exclusion chromatography

| Mode | ID | Parameter | Water (Average) | 0.1X PBS (Average) | 1X PBS (Average) |
|---|---|---|---|---|---|
| LS | Munster 151 | # particles (×10^11/mL) | 3.4 ± 0.4 | 0.4 ± 0 | 0.4 ± 0.0 |
| | | Mode size (nm) | 74.3 ± 10.7 | 64.7 ± 5.7 | 145 ± 29.1 |
| | | Poly-dispersity index | 4 ± 0.5 | 3.6 ± 0.2 | 3.5 ± 0.2 |
| FL | Munster 150 | # particles (×10^8/mL) | 1.6 ± 0.1 | 0.5 ± 0 | 0.8 ± 0.1 |
| | | Mode size (nm) | 17 ± 3.5 | 13.3 ± 3.2 | 21.3 ± 9.8 |
| | | Poly-dispersity index | 33.5 ± 1.9 | 29.9 ± 9 | 13.5 ± 4.6 |
| FL | Munster 151 | # particles (×10^8/mL) | 1.5 ± 1.5 | 0.9 ± 0.1 | 1.5 ± 0.3 |
| | | Mode size (nm) | 13.3 ± 0.6 | 43.7 ± 54 | 14.3 ± 2.5 |
| | | Poly-dispersity index | 25.4 ± 6.2 | 7.4 ± 1.3 | 16.1 ± 4.3 |

Since the NTA procedure is, by definition, a single particle analysis procedure, it has the associated strengths and limitations of all stochastic measurements. Measurement times (30-60 sec) were selected as a pragmatic compromise between managing the data volume and seeking data precision that represents the population sample as a whole. Necessarily, a small number of large (and hence comparatively immobile) particles can influence the statistics based both on their residence time in the field of view and on their light scattering properties. At a population level, NTA provides a size distribution analysis from which the mean, mode, median and other statistical parameters can be defined to summarize the number vs. size distribution. In this study, the algorithm used to represent the number vs. size distribution was the D90/D10 index—the particle diameter that encompassed that largest 10% of the particles and the diameter that encompassed the smallest 10% of the particles; the ratio of D90/D10 being a ‘poly-dispersity index’. A completely homogeneous population of particles with identical hydrodynamic diameters would have a poly-dispersity index of 1.0. It is acknowledged that this is only one measure of poly-dispersity that could be applied and that is it used simply as a surrogate of the complete particle size distribution curve (FIG. 3A).

As with all single particle detection/stochastic techniques such as PCS, FCS or FIDA, there are an optimal number of measured events per frame/field of view. Samples were diluted to yield a time average of ~50 particles per field of view—typically with a 200-2000 fold dilution of the microparticle sample when measuring total particles via light scatter. As such, microparticle numbers were on the order of $\sim 10^8$/mL in the field of view and thus $\sim 10^{11}$/mL prior to dilution of the microparticle sample.

Table 2, when measured under light scattering (LS) mode, shows an approximately 10-fold decrease in microparticles detected in the sample when performing the 1 mL serum chromatography in water ($\sim 3\times 10^{11}$ $mL^{-1}$) compared to PBS ($\sim 0.3\times 10^{11}$ $mL^{-1}$). Consistent with the $A_{280}$ values (FIGS. 2A-2C), the largest difference was observed between pure water and 10% v/v PBS—marginal differences were observed between 10% PBS and 100% PBS. The mode particle size appears to increase for samples isolated in PBS although the difference is not large and the D90/D10 poly-dispersity index is not significantly altered (range 3.5-4.1).

Nevertheless, from Table 2 the conclusion is that the reduced $A_{280}$ peak observed in FIGS. 2A-2C is associated with a corresponding reduction in microparticles with a hydrodynamic diameter of 50-150 nm when measured by NTA under light scattering mode.

The number of microparticles is operationally defined as the number of entities that scatter light (or fluoresce, see below) with a hydrodynamic diameter of 15-500 nm regardless of molecular composition or cellular origin.

Effect of Water and PBS on Microparticle Quantitation and Protein Concentration

Experiments similar to those described in Table 2, but with the exclusion of 10% PBS, were performed on a series of 6 additional 0.5 mL serum samples from GBM patients (Table 3). In this summary, the ratio of the # microparticles/mL (under light scatter) to the total protein content (μg/mL) is included. The units for this ratio are $ug^{-1}$ ($\times 10^8$).

For all 6 samples, isolation of microparticles in water yielded 4-5 fold higher # of microparticles when measured via light scattering NTA (~10-fold higher—Table 2). However, since the protein concentrations are 40-50 fold lower when isolating microparticles in PBS (Table 5), the ratio of the # particles/μg protein is ~10 fold higher in PBS.

The molecular basis for this difference is not immediately clear. However, as discussed previously and below, the microparticles measured may have a contribution from lipids, proteolipids and other components in addition to ‘cellular exosomes’. Some or all of these species may have solubility and aggregation properties that could well be affected by pH, ionic strength or specific salt interactions that could be markedly different between water, 10% PBS and PBS and could thus affect their properties on size exclusion chromatography and upon subsequent NTA measurement.

TABLE 3

Microparticle protein isolation from size-exclusion chromatography of 0.5 mL serum

| | # microparticles ($\times 10^{10}$/mL) | | Ratio # particles | Particles/protein ($ug^{-1}\times 10^8$) | | Ratio particles/protein |
|---|---|---|---|---|---|---|
| Sample ID | ddH20 | PBS | ($PBS/H_20$) | ddH20 | PBS | ($PBS/H_20$) |
| E43/E41 | 7.6 ± 1.2 | 1.5 ± 0.2 | 0.20 | 3.5 | 29.4 | 8.4 |
| E44/E35 | 8.6 ± 0.6 | 2.1 ± 0.0 | 0.24 | 2.5 | 35.6 | 14.2 |
| E45/E38 | 9.5 ± 0.1 | 1.1 ± 0.2 | 0.12 | 3.5 | 28.2 | 8.1 |

TABLE 3-continued

Microparticle protein isolation from size-exclusion chromatography of 0.5 mL serum

| | # microparticles ($\times 10^{10}$/mL) | | Ratio # particles | Particles/protein ($ug^{-1} \times 10^8$) | | Ratio particles/protein |
|---|---|---|---|---|---|---|
| Sample ID | ddH20 | PBS | (PBS/$H_2$0) | ddH20 | PBS | (PBS/$H_2$0) |
| E46/E39 | 8.5 ± 1.7 | 2.9 ± 0.2 | 0.34 | 3.3 | 30.2 | 9.2 |
| E53/E31 | 10.3 ± 0.3 | 2.5 ± 0.2 | 0.24 | 3.1 | 20.8 | 6.7 |
| E54/E32 | 8.8 ± 0.2 | 2.1 ± 0.2 | 0.24 | 3.2 | 27.3 | 8.5 |
| Mean | 8.9 | 2.0 | 0.23 | 3.2 | 28.6 | 9.2 |
| SD | 0.9 | 0.7 | 0.07 | 0.4 | 4.8 | 2.6 |

The LM10 NTA instrument and software can be operated in two modes—either without a band pass filter (light scattering mode) or with a band pass or other interference filter (fluorescence mode). In the current instrument configuration, a cut on filter is placed between the sample observation chamber and the CCD detector. This filter has the optical property such that it has a low transmittance below ~430 nm and a high transmittance at wavelengths above ~430 nm (however, the transition from low to high transmittance is not absolute at exactly 430 nm).

Figure 4A:
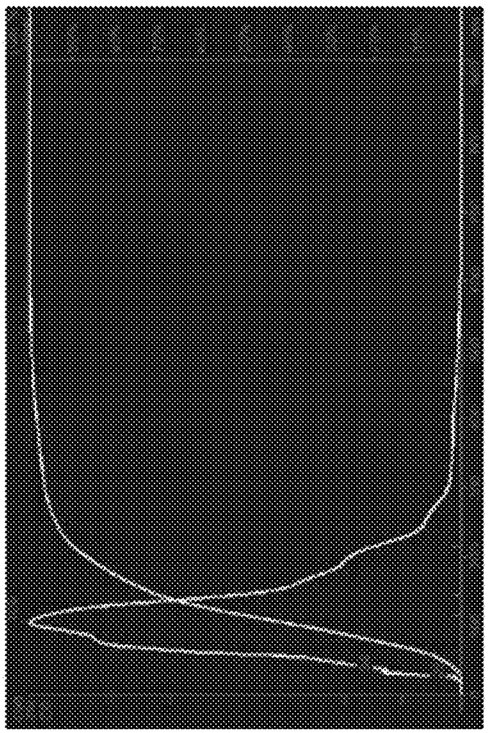
FIGS. 4A-4D relate to a control blue fluorescent microparticle analyzed by NTA in fluorescence mode.
Figure 4B:
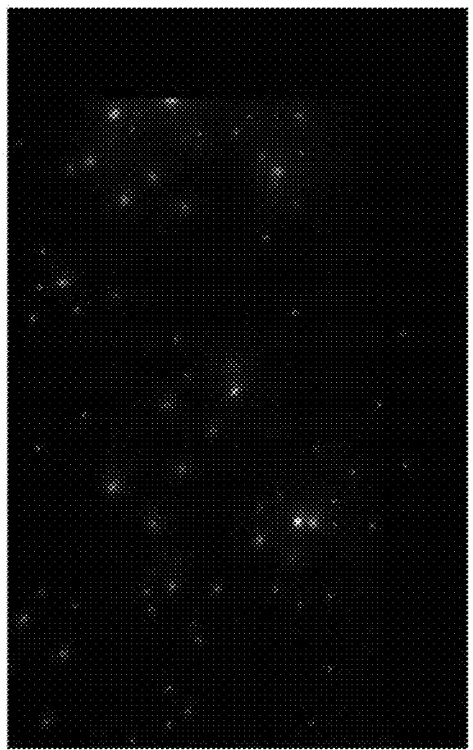
Figure 4C:
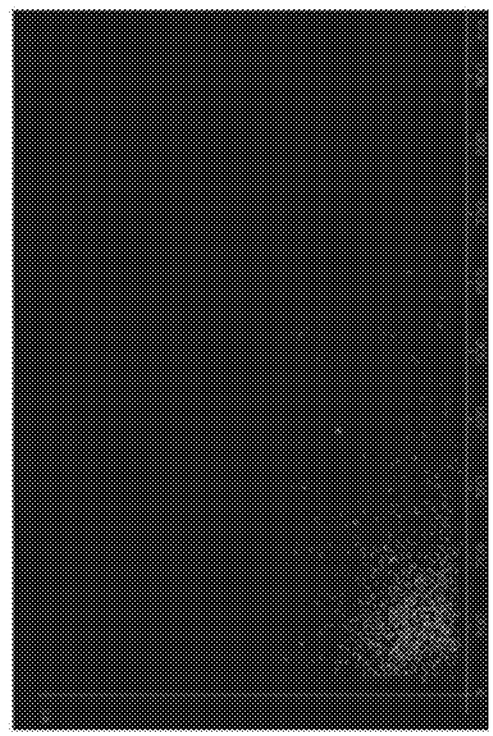
Figure 4D:
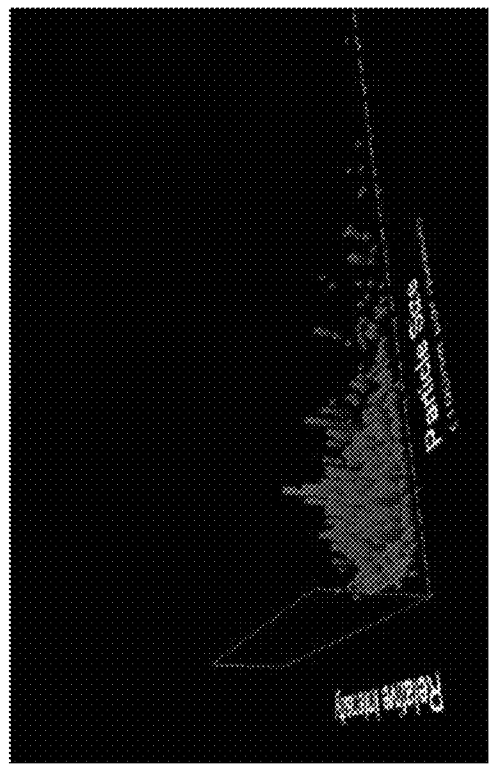
Figure 6A:
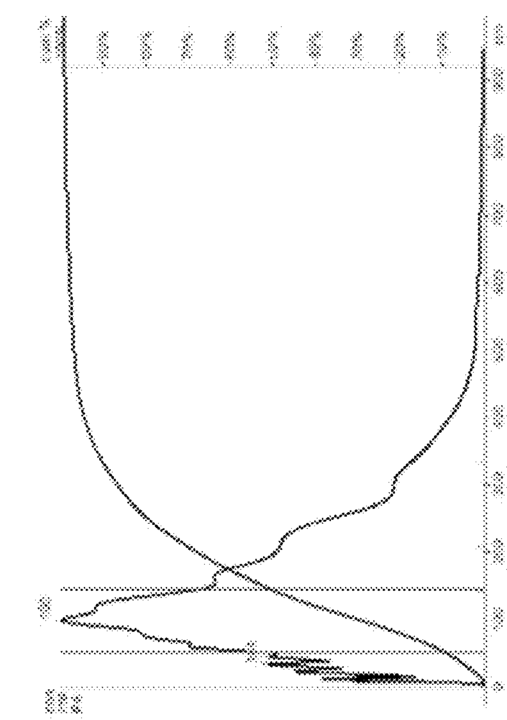
FIGS. 6A-6D relate to a PBS-processed patient sample analyzed by NTA in fluorescence mode, with the sample rendering a clear distribution of large microparticles with few small microparticles and a low polydispersity index.
Figure 6B:
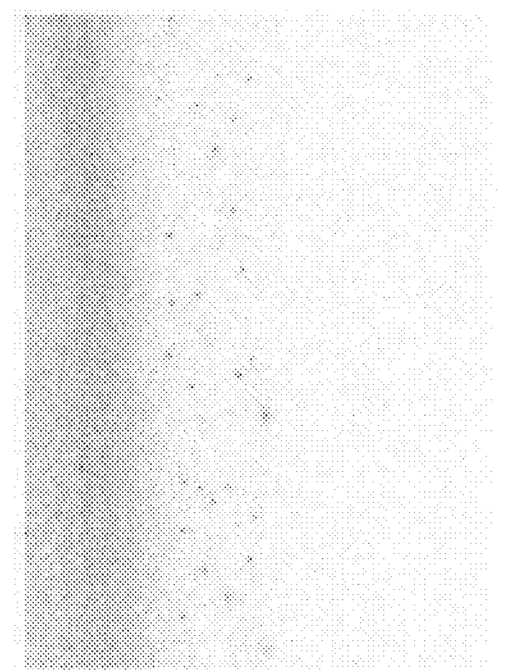
Figure 6C:
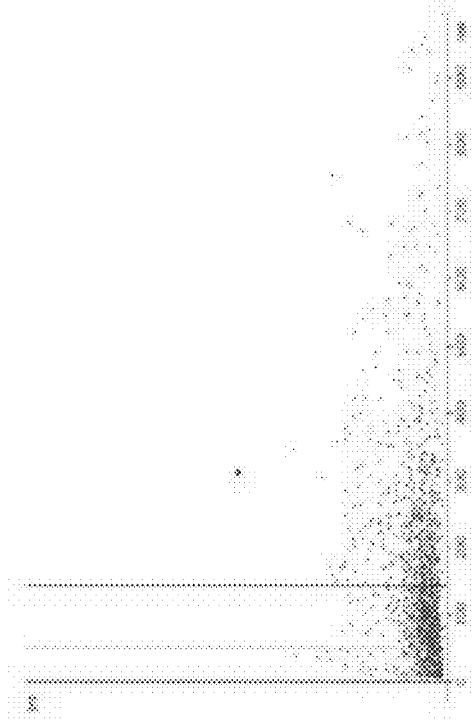
Figure 6D:
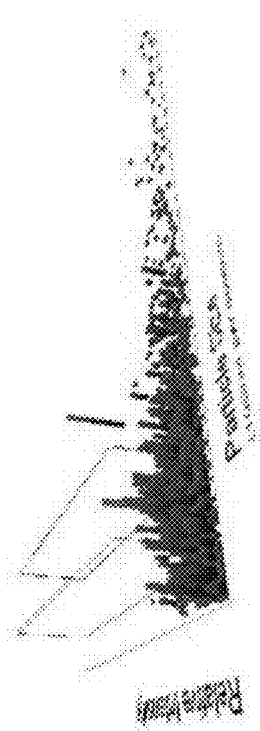
Figure 7A:
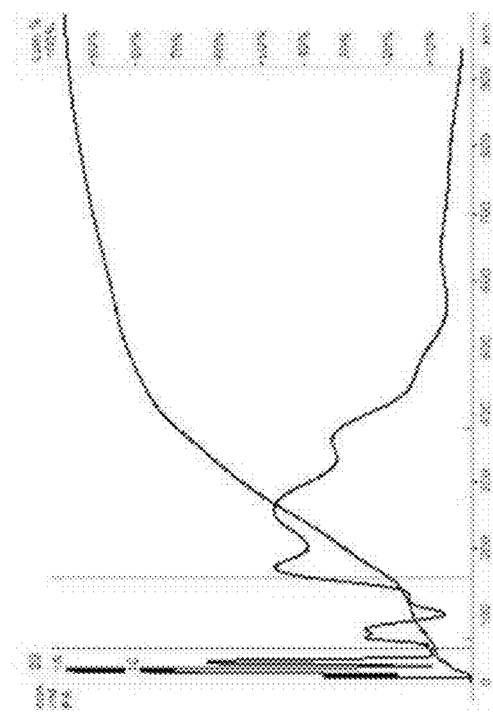
FIGS. 7A-7D relate to a water-processed patient sample analyzed by NTA in fluorescence mode, with the sample rendering a large number of small microparticles with a clear distribution of large microparticles and a high polydispersity index.
Figure 7B:
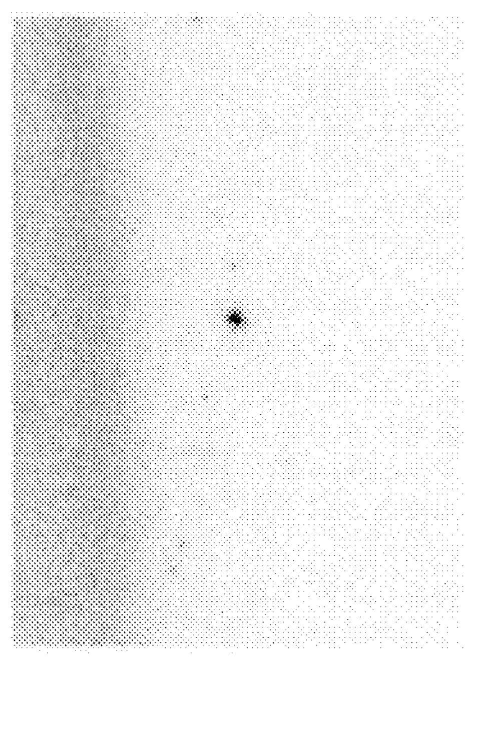
Figure 7C:
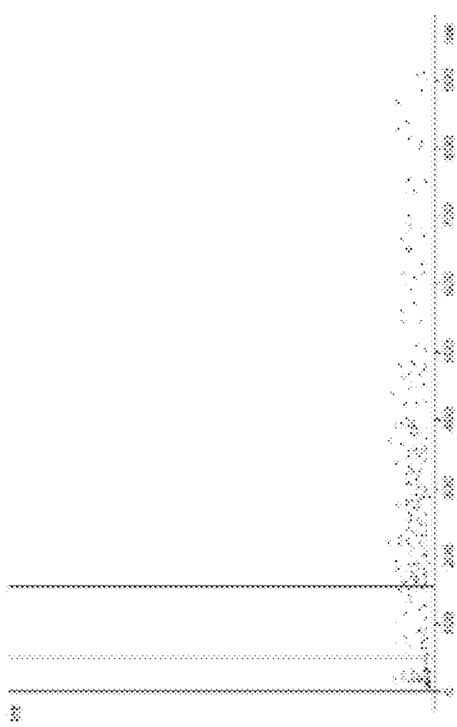
Figure 7D:
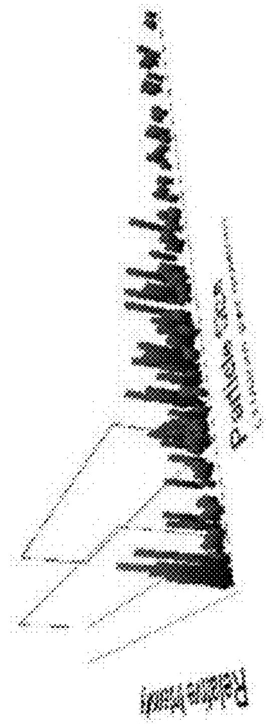
Figure 8B:
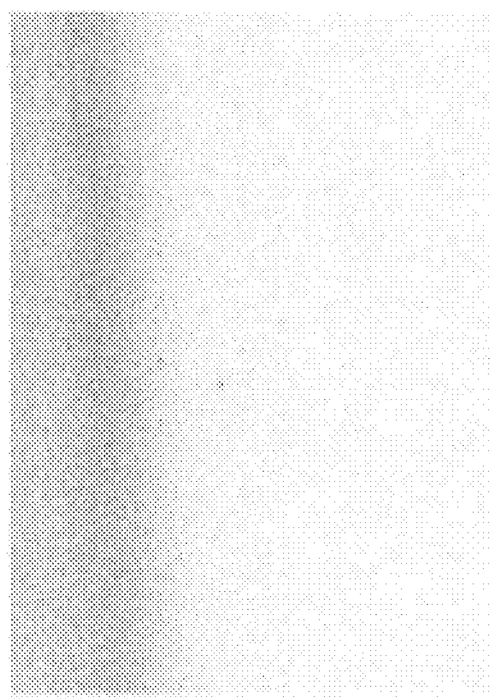
FIGS. 8A-8D relate to a water-processed patient sample analyzed by NTA in fluorescence mode, with the sample rendering a large number of small microparticles with a clear distribution of large microparticles and a high polydispersity index.
Figure 8D:
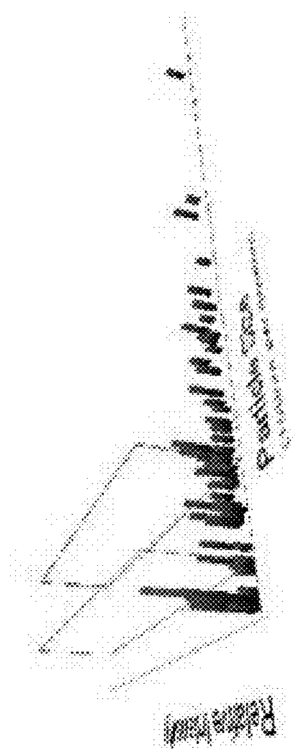
Figure 8A:
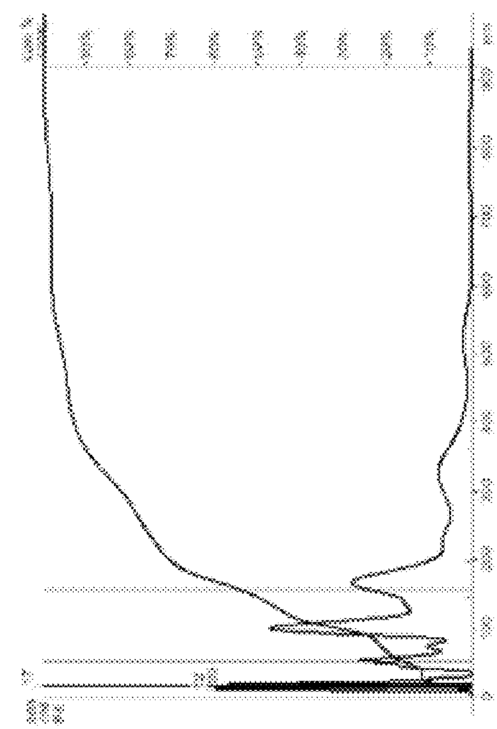
Figure 8C:
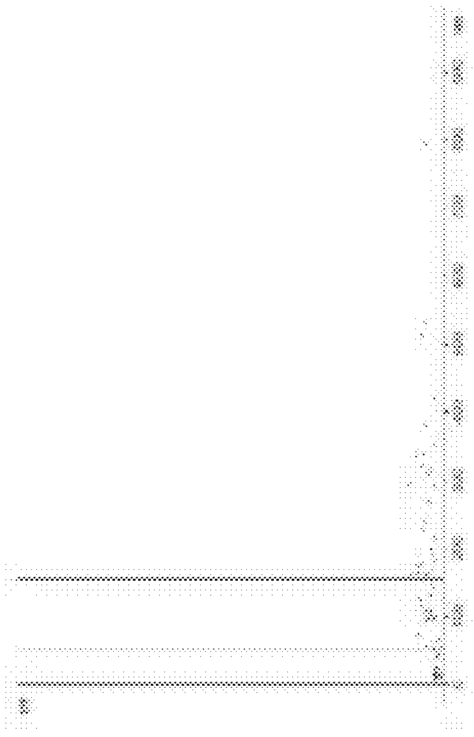
Figure 9B:
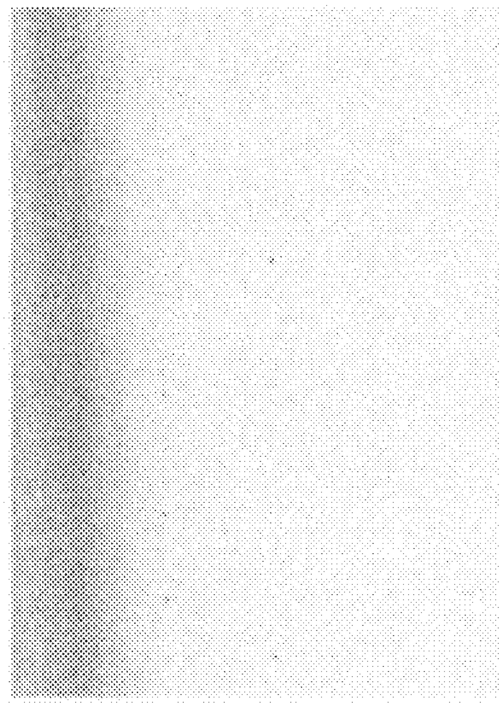
FIGS. 9A-9D relate to a water-processed patient sample analyzed by NTA in fluorescence mode, with the sample rendering a large number of small microparticles with no obvious distribution of large microparticles and a high polydispersity index.
Figure 9D:
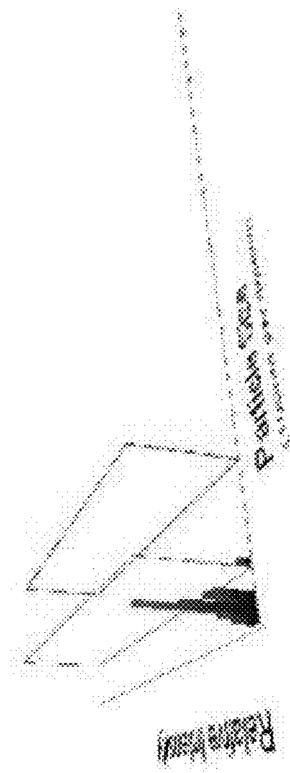
Figure 9A:
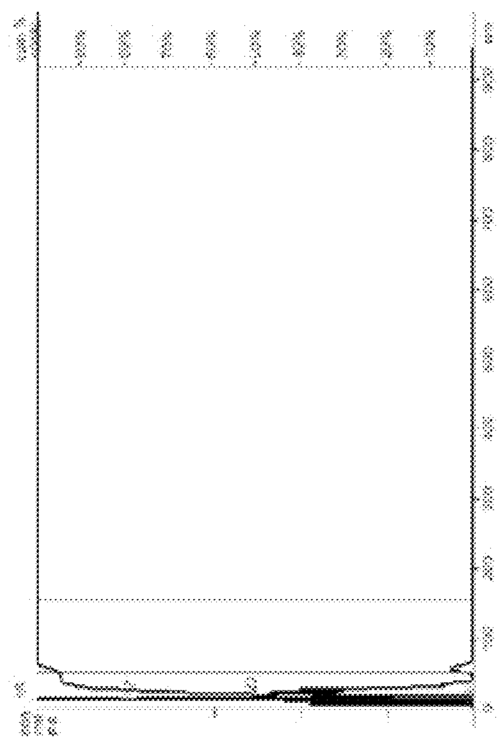
Figure 9C:
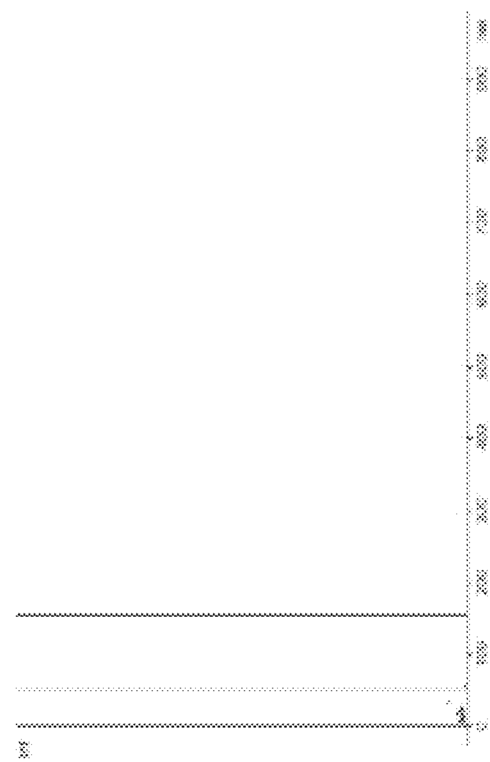

Nevertheless, in fluorescence mode with this cut on filter placed in the optical path, we were able to readily detect 100 nm fluorescent microspheres at a concentration of $\sim 10^8$ $mL^{-1}$ and which typically yielded a calculated hydrodynamic diameter of ~95-105 nm when measured at room temperature. A typical fluorescence particle distribution analysis summary is shown in FIGS. 4A-4C. Thus, we conclude that we can readily detect and quantify nanometer size extrinsic fluorophores with a large Stokes shift, good photostability and high quantum yield/extinction coefficient at a concentration of $\sim 10^8$ particles/mL.

Detection of Fluorescent Microspheres in GBM Patients

In FIG. 13, we summarize the data obtained when performing similar experiments on unlabeled microparticles isolated from GBM patients using either water (FIG. 13B) or PBS (FIG. 13A) as the mobile phase for size exclusion chromatography as indicated. We emphasize that light transmitted through the 430 nm cut on filter and detected by the CCD after excitation of the sample with a 405 nm laser (hereafter referred to as 'fluorescence') would only arise from an endogenous fluorophore within the microparticle since no extrinsic labeling has been performed (compare with Dragovic et al., (2011)).

In these experiments, we observed seemingly fluorescent microparticles in the samples—albeit at a very low ($\sim 10^8$/mL) concentration compared to the total number of (scattering) particles ($\sim 10^{10}$/mL). As such, when microparticle samples were analyzed, they were not pre-diluted from the aliquots obtained from the chromatography procedure (also referred to as 'neat').

Secondly, we observed that the apparent fluorescence seemingly suffered from photobleaching over time and thus a flow-based measurement was undertaken whereby the sample was injected into and out of the flow cell at a slow (nL/min) rate to 'replenish' the field of view with fresh ('unphotobleached') aliquots of microparticles. NTA analysis software which controls and accounts for sample flow was used. Finally, the optical path of the instrument used in these experiments had interference in the field of view that required a modification of the analysis procedure to remove this artifact. This necessarily compromised the quality of the resultant data. With these three major procedural and instrument modifications to the light scattering procedure, we obtained the data shown in FIG. 13.

Discussion

It is important to note that the mode size, particle number and poly-dispersity index (D90/D10) calculation shown for the fluorescence measurements in FIG. 13 are identical to those used for light scattering and are obtained from the NTA analysis software.

Specifically, for the data in this report, the NTA analysis software returns mode size and # particle values without any gating. For many samples we observed a large number of small (15-30 nm) particles within a comparatively tight distribution, and as such they are typically indicated as the mode (most common) particle size. This automated analysis to determine mode size does not account for larger (50-500 nm) microparticles that are present in most samples. The wide variety of both small and large fluorescent particles is reflected in the high D90/D10 poly-dispersity indices (>10 for most samples). For samples prepared in PBS, the mode value is sometimes the larger of the two populations of particles and hence in these cases, the automated analysis returns this particle size range as the automated value.

As a result of the limitations of the automated analysis as currently employed, we reviewed each fluorescence population file manually and qualitatively grouped them according to their size distribution (Table 5; see Data Appendix at end of Example 1) into 4 buckets. Example XPS reports and data descriptions are summarized in the Data Appendix.

Summary of Data

Microparticles with a mode hydrodynamic diameter of 50-100 nm were isolated using size exclusion chromatography and characterized using Nanoparticle Tracking Analysis (NTA) and BCA for microparticle size/number and protein content, respectively. Microparticles were obtained by chromatography using either $ddH_2O$ or PBS, pH 7.4 as the mobile phase. Endogenous fluorescence in the microparticles thus obtained was also assessed using NTA in the fluorescence detection mode ($\lambda_{ex}$=405 nm, $\lambda_{em}$>430 nm).

These results suggest that microparticles with a mode diameter of 50-100 nm measured by light scattering are present in GBM patient serum at a concentration of $\sim 10^{12}$ particles/mL serum when isolated using chromatography in $ddH_2O$. However, significantly (4-10-fold) fewer microparticles of this mode size are obtained when size exclusion chromatography is undertaken in PBS compared to water. Further, microparticles isolated in PBS appear to have a lower protein content compared to those isolated in water. The basis for this difference is not immediately apparent.

Microparticles of approximately these dimensions (albeit with a highly heterogeneous apparent size distribution from ~15-500+ nm) are observed under fluorescence mode. This implies that these microparticles contain an endogenous fluorophore that has fluorescence above 430 nm when excited at 405 nm. The number of these fluorescent microparticles appears to be <<1% of the total number of microparticles as measured by light scattering.

In conclusion, microparticles prepared from the serum of GBM patients that have taken Gliolan/5-ALA PO contain an endogenously fluorescent species that is observed in a small (<<1%) fraction of the total number of microparticles quantifiable at approximately 4-48 hours post dosing when isolated by size exclusion chromatography.

Table 4 outlines a summary of the data presented from the serum-isolated microparticles. The quantity of microparticles, their size, and the extent of fluorescence evaluated by NTA analysis are provided.

TABLE 4

Serum Microparticle Data Summary

| | Light Scattering | Fluorescence Mode | Notes |
|---|---|---|---|
| Particle # (Pre-operative) | 5.6 + 0.3 ($\times 10^{10}$/ml) | 3.3 + 0.7 ($\times 10^{8}$/ml) | N = 19 ($p < 0.01$) |
| Mode size (nm) | 56 +/− 21 | 46.5 +/− 10 | |
| 4 HR | 1.4 × $10^{10}$/ml | 0.8 × $10^{8}$/ml | 0.8 × $10^{8}$/ml @ 7+ HRS |
| Classical SEC Buffer # ($\times 10^{8}$) (N = 18) pre-operative | 2.04 × $10^{10}$/ml | 1.2 × $10^{8}$/ml | <1% Total Count ($p < 0.01$) |

Detailed Materials and Methods for Example 1

Materials

AB serum (Human serum from AB-blood-group-typed donors): Sigma Aldrich, St. Louis, Mo.

Bio-Rad Econom Column chromatography column, (2.5 cm ID×10 cm)

Micro BCA Protein Assay kit (Thermo Scientific)

PS beads: 100 nm polystyrene beads

2% cross-linked agarose (ABT, www.abtbeads.com, Florida, USA)

PBS: phosphate buffered saline, pH 7.4

GE AKTA Purifier 10 and FRAC 950 system (GE Healthcare, Piscataway, N.J.)

Size Exclusion Chromatography Parameters

TABLE 6

| System | Parameter | Setting |
|---|---|---|
| Bio-Rad Econo-Column chromatography column on a GE Healthcare AKTA 10 purifier | Step 1. Wash phase | 300 mL |
| | Step 2. Sample Load | 0.4-1 mL serum/plasma |
| | Step 3. Wash | 1 mL wash to complete drain by gravity |
| | Step 4. Wash | 1 mL wash to complete drain by gravity |
| | Step 5. Wash | 3 mL load |
| | Step 6. Isocratic elution | 2 mL/min for 30 min, collection periodicity: 0.5 min |
| UV Absorbance | UV absorbance collected | 280 nm (AU) |
| Conductivity | Conductivity | S/m |

TABLE 6-continued

| System | Parameter | Setting |
|---|---|---|
| Frac 950 fraction collector | Collect fractions (during isocratic elution step only) | 1 mL fractions collected for 30 min; total 60 fractions collected |

Clinical Samples

Serum study samples were provided by the Sponsor from Munster, Germany and Emory University, USA and received at DHMRI frozen on dry ice in ~1-2 mL aliquots. Once thawed on the bench at room temperature (~22° C.), 0.4-1 mL aliquots were processed to isolate microparticles as described below. The remaining sample, if any, was re-frozen and stored at −80° C.

Fluorescence NTA XPS Reports

In FIGS. 5-12 particle number (n) were generated directly by the NTA software—no gating was applied so all particles are counted equally across the range of size distributions. Mode (nm) was generated directly by the NTA software and refers to the most common size. Mean (nm) was generated directly by the NTA software and refers to the average of all values. D90/D10 was calculated from values obtained by the NTA software and refers to a measure of the breadth/dispersity of the sample. Qualitative peak refers to a qualitative assessment of where a second 'large' peak might occur if the software could find a bimodal distribution. "Category" refers to one of the 4 categories (or characteristics) subjectively selected (A-D).

Data Appendix

This appendix contains Table 5, which is referenced in the Results and Discussion section above

TABLE 5

Microparticle quantitation following size-exclusion chromatography in water vs PBS via fluorescence NTA with grouping of size distributions

| DHMRI ID | Particle #, n ($\times 10^{8}$/mL) | D90/D10 ratio | Mode (nm) | Mean (nm) | Qualitative peak (nm) | Classification |
|---|---|---|---|---|---|---|
| Pre-E3 | 4.43 | 2.7 | 267 | 261 | 267 | A (predominately large particles) |
| E54 | 1.66 | 19.5 | 25 | 243 | 180 | B (mixed population of large and small) |
| | 0.88 | 14.4 | 17 | 334 | 250 | B |
| | 0.98 | 10.7 | 20 | 342 | 250 | B |

TABLE 5-continued

Microparticle quantitation following size-exclusion chromatography in water vs PBS via fluorescence NTA with grouping of size distributions

| DHMRI ID | Particle #, n ($\times 10^8$/mL) | D90/D10 ratio | Mode (nm) | Mean (nm) | Qualitative peak (nm) | Classification |
|---|---|---|---|---|---|---|
| E53 | 1.00 | 16.8 | 18 | 262 | 200 | B |
| | 1.44 | 18.3 | 20 | 245 | 200 | B |
| | 1.02 | 14.4 | 24 | 373 | 250 | B |
| E52 | 0.43 | 17.2 | 12 | 292 | 192 | B |
| | 0.48 | 19.8 | 13 | 329 | 250 | B |
| | 0.51 | 12.2 | 13 | 304 | 200 | B |
| E51 | 0.46 | 6.2 | 14 | 208 | 191 | B |
| | 0.52 | 17.2 | 17 | 181 | 150 | B |
| | 0.37 | 12.3 | 9 | 186 | 125 | B |
| E50 | 0.46 | 3.1 | 15 | 22 | 15 | C (predominately small particles) |
| | 0.61 | 13.8 | 14 | 71 | 50 | C |
| | 0.29 | 14 | 11 | 178 | 150 | B |
| E49 | 0.25 | 4.6 | 13 | 470 | 200 | B |
| | 0.31 | 5.0 | 215 | 443 | 215 | A |
| | 0.29 | 5.2 | 246 | 474 | 246 | A |
| E48 | 0.36 | 3.7 | 13 | 23 | 15 | C |
| | 0.03 | 1.2 | 87 | 87 | 87 | C |
| | 0.06 | 17.9 | 11 | 118 | 104 | B |
| E47 | 0.60 | 7.9 | 12 | 37 | 15 | C |
| | 0.32 | 4.8 | 18 | 23 | 20 | C |
| | 0.48 | 7.0 | 15 | 41 | 20 | C |
| E46 | 0.92 | 14.2 | 22 | 308 | 250 | B |
| | 0.49 | 5 | 18 | 332 | 250 | B |
| | 0.46 | 5 | 29 | 359 | 230 | B |
| E45 | 1.02 | 8.3 | 22 | 84 | 80 | B |
| | 0.54 | 10 | 12 | 119 | 100 | B |
| | 0.21 | 4.0 | 76 | 129 | 100 | B |
| E44 | 0.84 | 18.9 | 12 | 249 | 170 | B |
| | 1.4 | 13 | 21 | 134 | 150 | B |
| | 0.92 | 17 | 14 | 326 | 200 | B |
| E43 | 0.65 | 14 | 14 | 320 | 200 | B |
| | 0.68 | 8.2 | 13 | 312 | 180 | B |
| | 1.23 | 7.7 | 20 | 350 | 300 | B |
| E42 | 1.46 | 20 | 12 | 302 | 200 | B |
| | 0.72 | 5.5 | 209 | 372 | 209 | A |
| | 0.89 | 4.6 | 249 | 331 | 249 | A |
| E41 | 1.42 | 14 | 14 | 245 | 200 | B |
| | 1.19 | 6.7 | 144 | 263 | 144 | A |
| | 0.81 | 4.3 | 148 | 294 | 148 | A |
| E40 | 0.78 | 14.6 | 13 | 396 | 280 | B |
| | 1.08 | 8.2 | 10 | 473 | 250 | B |
| | 1.6 | 15.9 | 28 | 292 | 290 | B |
| E39 | 2.12 | 6.6 | 234 | 381 | 234 | A |
| | 3.43 | 6.2 | 90 | 153 | 90 | A |
| | 3.72 | 6.1 | 100 | 182 | 100 | A |
| E38 | 1.18 | 6.1 | 160 | 278 | 160 | A |
| | 1.11 | 5.4 | 185 | 284 | 185 | A |
| | 1.41 | 6.5 | 200 | 250 | 200 | A |
| E37 | 0.67 | 18 | 10 | 128 | 100 | B |
| | 0.74 | 15 | 21 | 104 | 140 | B |
| | 0.46 | 5.8 | 193 | 313 | 193 | A |
| E36 | 0.27 | 13.2 | 8 | 342 | 200 | B |
| | 0.86 | 9.2 | 19 | 86 | 100 | B |
| | 0.68 | 6.9 | 12 | 391 | 227 | B |
| E35 | 1.86 | 5.4 | 159 | 264 | 159 | A |
| | 1.45 | 4.2 | 157 | 288 | 157 | A |
| | 1.58 | 5.7 | 215 | 271 | 215 | A |
| E34 | 0.28 | 5.2 | 14 (195) | 388 | 195 | B (A) |
| | 0.17 | 5.2 | 18 (349) | 440 | 349 | B (A) |
| | 0.23 | 6.7 | 13 (239) | 310 | 239 | B (A) |
| E33 | 0.86 | 4.5 | 226 | 413 | 226 | A |
| | 0.87 | 4.3 | 348 | 454 | 348 | A |
| | 0.70 | 3.2 | 215 | 422 | 215 | A |
| E32 | 1.63 | 5.4 | 223 | 367 | 223 | A |
| | 1.33 | 4.8 | 239 | 383 | 239 | A |
| | 1.39 | 5.0 | 326 | 416 | 326 | A |
| E31 | 1.83 | 8.1 | 32 (293) | 398 | 293 | B (A) |
| | 1.76 | 6.4 | 21 (190) | 399 | 190 | B (A) |
| | 1.69 | 6.9 | 16 (348) | 403 | 348 | B (A) |
| E30 | 1.83 | 16 | 12 | 154 | 100 | B |
| | 1.51 | 11.7 | 17 | 339 | 200 | B |
| | 1.28 | 20.4 | 14 | 344 | 180 | B |

TABLE 5-continued

Microparticle quantitation following size-exclusion chromatography in water vs PBS via fluorescence NTA with grouping of size distributions

| DHMRI ID | Particle #, n ($\times 10^8$/mL) | D90/D10 ratio | Mode (nm) | Mean (nm) | Qualitative peak (nm) | Classification |
|---|---|---|---|---|---|---|
| E29 | 0.67 | 10.8 | 27 (97) | 286 | 97 | B |
| | 0.92 | 22.3 | 11 | 238 | 150 | B |
| | 2.13 | 9.7 | 179 | 247 | 179 | A |
| E28 | 0.85 | 6.7 | 13 | 545 | 280 | B |
| | 0.96 | 10 | 23 | 475 | 350 | B |
| | 0.87 | 10 | 21 | 307 | 200 | B |
| E27 | 0.59 | 42 | 11 | 414 | ? | D (long 'tail') |
| | 0.52 | 37 | 10 | 335 | ? | D |
| | 0.54 | 29 | 10 | 298 | 300? | D |
| E26 | 1.66 | 26.5 | 15 | 432 | 200? | D |
| | 1.38 | 28 | 12 | 343 | ? | D |
| | 1.44 | 26 | 13 | 420 | 200? | D |
| E25 | 1.07 | 32 | 10 | 287 | ? | D |
| | 1.05 | 32 | 10 | 296 | ? | D |
| | 1.11 | 31 | 14 | 307 | ? | D |

The characteristics shown in Table 5 are described below:

Type A Characteristics:

Few small (10-30 nm) particles, clear distribution of large particles (typically 100-300 nm), mean and mode diameter comparable (within 2-fold), low D90/D10 (<10, typically 4-7), often associated with a high particle number (typically >$1.0\times10^8$/mL) and PBS elution buffer.

Type B Characteristics:

Large number of small (10-50 nm) particles, clear distribution of large particles (typically 100-500 nm), mean and mode diameter significantly different (typically >10-fold), high D90/D10 (typically 10-20), often associated low or medium particle number (typically $0.5\text{-}1.0\times10^8$/mL). Seen with both PBS, and in particular, with water as elution buffer.

Type C Characteristics:

Large number of small (10-50 nm) particles, no obvious distribution of large particles, mean and mode diameter comparable (and small), high D90/D10 (typically 10-20), often associated low or medium particle number (typically $0.5\text{-}1.0\times10^8$/mL) and water as elution buffer.

Type D Characteristics:

Large number of small (10-50 nm) particles, no obvious distribution of large particles, mean and mode diameter comparable (and small), very high D90/D10 (typically 20-40), often associated low or medium particle number (typically $0.5\text{-}1.0\times10^8$/mL) and water or 10% PBS as the elution buffer.

Example 2: U87 Cell Line Converts 5-Ala to PPIX Via a CPDX-Mediated Conversion Process which can be Monitored in Shed Microparticles This example demonstrates that U87 cell cultures actively convert 5-ALA to PPIX, that these cells produce coproporphyrinogen III oxidase (CPDX protein), and that CPDX proteins and PPIX are present in shed microparticles in cancer cell lines.

In Vitro Studies in U87

U87 cells representative of GBM tumors grown in T-75 flasks, in the absence of serum, were exposed to 5-aminolevulinic acid (5-ALA; 250 μg/ml) for 4 or 24 hours. Following exposure, cells were subjected to fluorescent excitation in a LSRII flow cytometer with an excitation at 406 nM violet wave length. Filter specifications were set at either 450/50, or set at 610/20 for the detection of protoporphyrin IX (PPIX).

Figure 14:
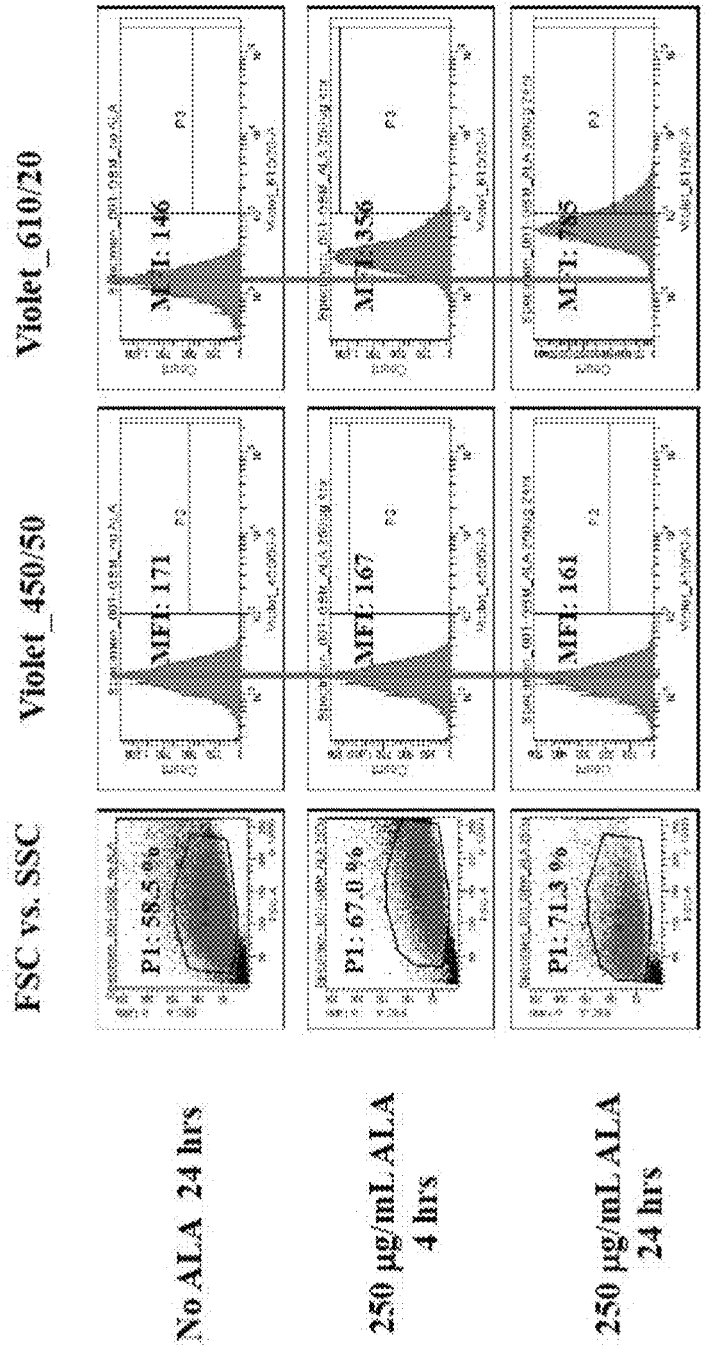
FIG. 14 shows the results of flow cytometry experiments to detect PPIX levels in untreated U87 cells, cells treated with 5-ALA for 4 hours, and cells treated with 5-ALA for 24 hours.

It was found that the mean fluorescence index (MFI), as a function of time, did not change in the absence of 5-ALA. In contrast, MFI increased following exposure to 5-ALA observed at 4 hours and 24 hours after exposure to 5-ALA (FIG. 14). These data indicate the temporal appearance of PPIX as a metabolic product from the conversion of 5-ALA to its metabolite as a product of cellular metabolism in the heme biosynthesis pathway.

Cancer Cell-Derived Microparticles Accumulate CPDX

The enzyme coproporphyrinogen III oxidase (CPDX) is involved in heme porphyrin metabolism. To investigate whether this enzyme is present in shed cancer cell-derived microparticles and to explore a role for this enzyme in the metabolic conversion of 5-ALA to PPIX, protein analysis was conducted on cancer cell-derived microparticle protein samples.

Microparticles in the conditioned media were recovered from culture supernatants using one of the Venceremin peptides (New England Peptide, Gardner Mass.). To recover microparticles, the Venceremin peptide Vn96reverse, referred to as Heladonin (Hdn; H2 N-LKLFEGLT-LAGWSFRSLSLGRGKGQSP-OH), and the scrambled peptide NDN were used. U87 (GBM) and HELA cells were cultured in an Integra bioreactor and lower chamber supernatant samples (2 mls) were harvested and mixed with 10 μl of protease inhibitor and 50 μg of Hdn peptide stock solution. Microparticles were prepared from bioreactor supernatant samples and analyzed in a western blot for the presence of CPDX. Additional aliquots of conditioned medium were exposed to ExoQuick (SBI, Systems Biology) for the isolation of shed microparticles. Total protein from the cell lysate of MFC7 and K562 cell lines was also analyzed. Table 7 provides a legend of the source of the protein sample analyzed in each lane as shown in FIG. 14.

TABLE 7

Identification of Protein Source in the Specified Blot Lanes

| Lane # | Protein Sample from: |
|---|---|
| 1 | GBM cells isolated with Hdn peptide |
| 2 | GBM cells isolated with Ndn peptide |

TABLE 7-continued

Identification of Protein Source in the Specified Blot Lanes

| Lane # | Protein Sample from: |
|---|---|
| 3 | GBM cells isolated with ExoQuick |
| 4 | HELA cells isolated with Hdn peptide |
| 5 | HELA cells isolated with Ndn peptide |
| 6 | HELA cells isolated with ExoQuick |
| 7 | MCF7 cell lysate |
| 8 | K562 cell lysate |

Figure 15:
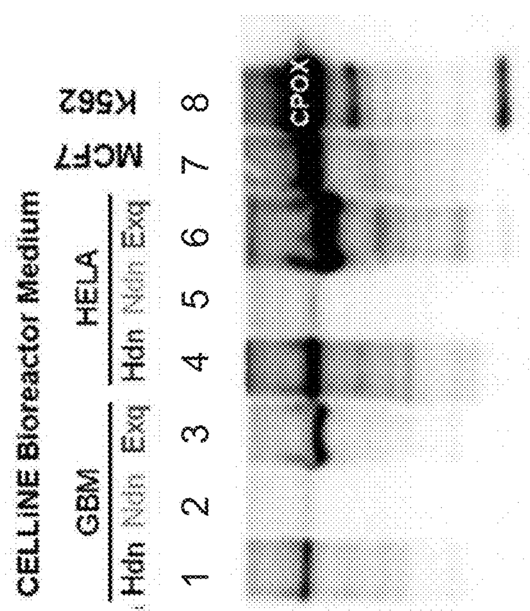
FIG. 15 is a Western blot showing that CPDX is found in cancer-derived microparticles.

As can be seen in FIG. 15, microparticles isolated from both GBM and HELA cell lines accumulated a CPDX protein as seen in the western blot probed with an anti-CPDX antibody. Samples isolated with the nonspecific Ndn peptide did not accumulate CPDX protein. These data demonstrate the presence of CPDX enzyme in microparticles shed from cancer cells. Without wishing to be bound by theory, it is believed that CPDX is involved in the conversion of 5-ALA to PPIX in microparticles. These data further reveal the ability to track intra-mitochondrial biomarkers (CPDX) in microparticles involved in the conversion of 5-ALA to PPIX and suggest the use of CPDX as a biomarker for tumor cells.

Example 3: Detection of GBM by Administration of Gliolan™

A patient is treated for GBM by surgical resection, external beam radiation, and temozolomide.

Per hospital standard protocol, the patient is evaluated on a regular basis (monthly) for clinical symptoms of disease recurrence with observational and MM evaluation for GBM recurrence.

Gliolan™ (5-ALA) is administered at a dosage of 20 mg/kg three hours prior to the time scheduled for the blood draw.

Blood is drawn and allowed to coagulate to produce serum or spun at 1000 g for 5 minutes to produce plasma. The biological fluid is frozen at −80 C and preserved for later processing. Microparticles are isolated using size exclusion chromatography with 2% agarose as the solid phase. Double distilled $H_2O$, (100% v/v) or PBS is used as mobile phase with a serum or plasma load volume <2% of bed volume and elution separation for molecular weight entities validated with protein standards.

5-ALA-mediated fluorescence associated with these microparticles is detected using a NTA analysis procedure (Nanosight Ltd, Wiltshire, UK).

What is claimed is:

1. A method for detecting a tumor, wherein the method comprises (a) administering a pharmaceutical composition comprising 5-aminolevulinic acid (5-ALA) to a subject;

(b) isolating tumor-derived microparticles from a biological sample from the subject; and (c) detecting a level of conversion of 5-ALA to protoporphyrin IX (PPIX) associated with the tumor-derived microparticles in the biological sample from the subject, thereby detecting the tumor, wherein the tumor is selected from the group consisting of ovarian, breast, pancreatic, prostate, lung, colorectal, renal and bladder tumor.

2. The method of claim 1, wherein the subject was previously treated for a tumor selected from the group consisting of ovarian, breast, pancreatic, prostate, lung, colorectal, renal and bladder tumor.

3. The method of claim 1, wherein the biological sample is whole blood.

4. The method of claim 1, wherein the biological sample is plasma or serum.

5. The method of claim 1, wherein the pharmaceutical composition is Gliolan™.

6. The method of claim 1, wherein the pharmaceutical composition comprising 5-ALA is administered orally.

7. The method of claim 1, wherein the pharmaceutical composition comprising 5-ALA is administered intratumorally.

8. The method of claim 1, wherein the pharmaceutical composition comprises 5-ALA at a concentration of 5 mg/kg, 10 mg/kg, 20 mg/kg or 30 mg/kg.

9. The method of claim 1, wherein the pharmaceutical composition comprising 5-ALA is administered for three, four, or five hours.

10. The method of claim 1, wherein the level of conversion of 5-ALA to PPIX is detected by measuring fluorescence.

11. The method of claim 1, wherein the level of conversion of 5-ALA to PPIX is detected by measuring the level of a metabolite along the 5-ALA to PPIX conversion pathway.

12. The method of claim 1, wherein the level of conversion of 5-ALA to PPIX is detected by measuring the level of a converting enzyme.

13. The method of claim 12, wherein the converting enzyme is coproporphyrinogen oxidase (CPDX).

* * * * *